US009045506B2

(12) United States Patent
Li et al.

(10) Patent No.: US 9,045,506 B2
(45) Date of Patent: Jun. 2, 2015

(54) DIPHOSPHONATE COMPOUND AND A METHOD FOR PREPARING THE SAME AND AN APPLICATION OF THE SAME

(75) Inventors: Mingqi Li, Chengdu (CN); Han Wang, Chengdu (CN); Qimin Deng, Chengdu (CN); Zuoyong Cheng, Chengdu (CN); Maoliang Li, Chengdu (CN); Yonglong Zeng, Chengdu (CN); Xue Jiang, Chengdu (CN); Yuchun Duan, Chengdu (CN); Sanping Zhu, Chengdu (CN); Dezhong Wen, Chengdu (CN)

(73) Assignee: Chengdu Yunke Pharmaceutical Co., Ltd. (CN)

( * ) Notice: Subject to any disclaimer, the term of this patent is extended or adjusted under 35 U.S.C. 154(b) by 0 days.

(21) Appl. No.: 13/880,972

(22) PCT Filed: Aug. 24, 2011

(86) PCT No.: PCT/CN2011/078808
§ 371 (c)(1),
(2), (4) Date: Apr. 22, 2013

(87) PCT Pub. No.: WO2012/058976
PCT Pub. Date: May 10, 2012

(65) Prior Publication Data
US 2013/0211097 A1    Aug. 15, 2013

(30) Foreign Application Priority Data
Nov. 3, 2010   (CN) .......................... 2010 1 0529957

(51) Int. Cl.
C07F 9/6541   (2006.01)
C07F 9/547    (2006.01)
C07F 9/40     (2006.01)

(52) U.S. Cl.
CPC ............ *C07F 9/6541* (2013.01); *C07F 9/4031* (2013.01); *C07F 9/5475* (2013.01)

(58) Field of Classification Search
CPC ........................... C07F 9/5475; C07F 9/6541
See application file for complete search history.

(56) References Cited

U.S. PATENT DOCUMENTS 5,442,101 A    8/1995   Hanhijarvi et al.

FOREIGN PATENT DOCUMENTS

CN       1062533 A      7/1992

OTHER PUBLICATIONS

International Search Report & English Translation Dated Nov. 4, 2011; Application No. PCT/CN2011078808.
Abdou, Wafaa M. et al., Synthesis, properties, and perspectives of gem-diphosphono substituted-thiazoles, European Journal of Medicinal Chemistry, 2008, vol. 43, No. 5, pp. 1015-1024.
Hudock, Michael P., Inhibition of *Trypanosoma cruzi* Hexokinase by Bisphosphonates, Journal of Medicinal Chemistry, 2006, vol. 49, pp. 215-223.

*Primary Examiner* — Joseph Kosack
(74) *Attorney, Agent, or Firm* — Andrew D. Fortney; Central California IP Group, P.C.

(57) ABSTRACT

The present disclosure relates to a new diphosphonate compound, and the method to prepare the above new diphosphonate compound. The new diphosphonate compound exhibits an activity in inhibiting osteoclast equivalent to alendronate sodium, and a higher activity in affecting the proliferation of osteoplast than the positive control compounds, but the positive control exhibits a weaker effect on osteoblast proliferation. In experimental examples, an administration schedule for the diphosphonate compound is provided.

19 Claims, No Drawings

DIPHOSPHONATE COMPOUND AND A METHOD FOR PREPARING THE SAME AND AN APPLICATION OF THE SAME

TECHNICAL FIELD

The present invention relates to a new diphosphonate compound, and to a method to prepare the above new diphosphonate compound.

BACKGROUND

Bone metabolic diseases are disorders of bone formation, bone resorption and deposition of bone minerals caused by disturbance of normal bone metabolism from congenital or acquired factors. Bone metabolic diseases include osteoporosis, vitamin D deficiency, vitamin C deficiency, renal osteodystrophy, etc. Among these bone metabolic diseases, osteoporosis is a common and frequent disease. Osteoporosis is a systematic and systemic bone disease characterized by brittleness increase of bone and high risk of fracture caused by bone loss, bone tissue microstructure destruction. As living standard of people continuously improves, life span of people prolongs and aging society comes, osteoporosis has become a common and frequent disease that seriously threatens health of the middle and old aged; particularly for menopause women, the balance of bone formation and bone resorption is disturbed by variation in estrogen level, resulting in massive bone loss, increase of bone resorption and/or descent of bone formation, causing osteoporosis, and even worse, osteoporotic fracture.

China is not only the country having the largest amount of population, but also the country having the largest amount of osteoporosis patients. Based on the fifth nationwide census, the male incidence of osteoporosis is 14.6% and the female incidence of osteoporosis is 61.8% in the old-aged above 60 years old, with an overall incidence of 6.97% and totally 88.26 million of middle and old aged threatened by occurrence of osteoporosis. To Mid 21 Century, China will come into the peak period of the aged society, the population above 60 constitutes 27% of the total population, reaching up to 400 million. As a result, the research and development on the drugs to prevent and treat osteoporosis have a great sense in improving the health of people and increasing life quality and also have a great social value.

Currently, the drugs used for treating osteoporosis mainly include four classes: one is bone resorption inhibitors such as a variety of diphosphonate compounds, Isopropyl isoflavones, calcitonin, estrogen and selective estrogen receptor modulator; one is bone formation-accelerating drugs such as fluoride, parathyroid hormone, insulin-like growth factor, protein synthetic hormone; one is ossification-accelerating drugs such as calcium, vitamin D and its derivatives; one is drugs for inhibiting the activity of osteoclast and enhancing bone formation such as strontium ranelate; and other classes such as traditional Chinese medicine.

Among the drugs for treating osteoporosis, diphosphonate drugs inhibiting bone resorption are the most commonly used. Diphosphonate drugs, i.e. pharmaceutically-acceptable salts, are synthetic analogue of natural pyrophosphate, having the basic structure shown in formula I:

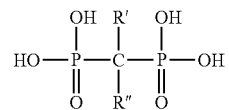

As shown in formula I, R', R'' lateral chains in diphosphonate molecular structure may affect its bone affinity. Typically, R' is H, OH or halogen and the like groups, R' has a smaller influence on the bone affinity of diphosphonate drugs; and the structure of R'' is a main factor that affects the bone affinity of diphosphonate drugs. Currently, based on different structures of R'', commercially available diphosphonate drugs generally include the following three classes: the first is that R'' is diphosphonate salt not comprising nitrogen, represented by Etidronate, clodronate, and clinically applied in the 70s last century; the second is that R'' structure comprises amino group, having a stronger ability of inhibiting bone resorption than the diphosphonate drugs without nitrogen, represented by Panidronate, alendronate. The third is that R'' is diphosphonate salt comprising nitrogen containing heterocycle, having an even stronger ability of inhibiting bone resorption and an easier clinical application, represented by Zoledronate which has a bone affinity over 10000 times stronger than Etidronate. Diphosphonate drugs comprising N (comprising —$NH_2$ or comprising N heterocycle) or not comprising N both treat osteoporosis through inhibiting the activity of osteoclast and have a weak effect on osteoblast proliferation. Although commercially available diphosphonate drugs have a more and more stronger effect on inhibiting osteoclast but also increase the risk of fracture, and moreover it has not reported that diphosphonate drugs have effect on osteoblast proliferation.

SUMMARY OF THE INVENTION

The object of the present invention is to overcome the deficiency that currently available diphosphonate compounds have strong effect on inhibiting the activity of osteoclast but weaker effect on osteoblast proliferation, and to provide a new diphosphonate compound and a method for preparing the same. The diphosphonate compound provided in the present invention is capable of bi-directionally regulating osteoblast and osteoclast.

The diphosphonate compound provided in the present invention has the structure of formula II:

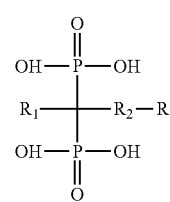

wherein R is

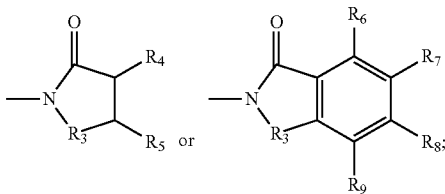

wherein $R_1$ is H, OH or halogen;

$R_2$ is

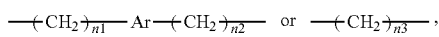

wherein $n_1=1\sim10$, $n_2=0\sim10$, $n_3=1\sim10$; if $n_1$, $n_2$ or $n_3 \geq 1$, the alkyl may be substituted by halogen, —CN, —$NO_2$ or —OH; Ar is aryl or substituted aryl, the substituent is C1~C6 alkyl, C1-C6 substituted alkyl, halogen, —CN, —$NO_2$ or —OH;

$R_3$ is Se or S;

$R_4$ and $R_5$ are independently selected from the group consisting of Hydrogen, halogen, —CN, —$NO_2$, —OH, —OR', —COOR', —OCOOR', —COR', —CON(R')$_2$, —OCON(R')$_2$, —SR, —$SO_2$R, —$SO_2$N(R')$_2$, —SOR' group, C1~C10 alkyl, C1~C10 substituted alkyl, alkenyl, substituted alkenyl, alkynyl, substituted alkynyl, aryl or substituted aryl, wherein each of R and R' is independently selected from the group consisting of H, alkyl, aryl, substituted alkyl or substituted aryl; $R_4$ and $R_5$ may also constitute 3~7 carbons of cyclo alkane, the cyclo alkane may be substituted by C1~C6 alkyl, C1~C6 substituted alkyl, halogen, —CN, —$NO_2$ or —OH;

$R_6$, $R_7$, $R_8$ and $R_9$ are independently selected from the group consisting of Hydrogen, halogen, —CN, —$NO_2$, —OH, —OR', —COOR', —OCOOR', —COR', —CON(R')$_2$, —OCON(R')$_2$, —SR, —$SO_2$R, —$SO_2$N(R')$_2$, —SOR' group, alkyl, alkenyl, alkynyl, aryl, substituted alkyl, substituted alkenyl, substituted alkynyl or substituted aryl, wherein each of R and RI's independently selected from H, alkyl, aryl, substituted alkyl or substituted aryl.

In the diphosphonate compound having the above formula II, $R_2$ is

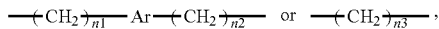

wherein $n_1=1\sim10$, $n_2=0\sim10$, $n_3=1\sim10$, Ar is aryl or substituted aryl, the substituent is halogen, —CN, —$NO_2$ or —OH;

$R_3$ is Se or S;

$R_4$ and $R_5$ are independently selected from the group consisting of Hydrogen, halogen, —CN, —$NO_2$, —OH or C1~C10 alkyl;

$R_6$, $R_7$, $R_8$ and $R_9$ are each independently selected from the group consisting of Hydrogen, halogen, —CN, —$NO_2$ or —OH alkyl.

In the diphosphonate compound having the above formula II, $R_1$ is preferably H, OH.

$R_1$ may also be halogen, preferably F, Cl or Br.

In the diphosphonate compound having the above formula II, $R_2$ is

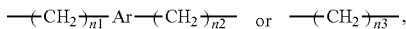

wherein $n_1=1\sim4$, $n_2=0\sim1$, $n_3=1\sim5$, Ar is aryl or substituted aryl, the substituent is halogen, —CN, —$NO_2$ or —OH.

In the diphosphonate compound having the above formula II, $R_2$ is

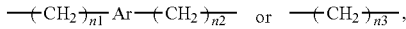

wherein $n_1=1\sim4$, $n_2=0\sim1$, $n_3=1\sim5$, Ar is aryl, preferably phenyl.

In the diphosphonate compound having the above formula II, $R_2$ is

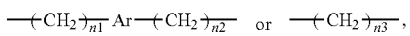

wherein Ar is substituted aryl, the substituent is C1~C6 alkyl substituted in different sites, C1~C6 optionally substituted alkyl, halogen, —CN, —$NO_2$ or —OH.

In the above compounds, $R_3$ is preferably Se.

In the diphosphonate compound having the above formula II, $R_6$, $R_7$, $R_8$ and $R_9$ are preferably hydrogen.

The present invention also provides two methods for preparing the diphosphonate compound having the above formula II.

One method for preparing the diphosphonate compound having the above formula II, comprising:

(1). Proton activation of methylene:

Tetraisopropyl methylene diphosphonate and NaH are performed with the proton activation reaction of methylene for 1 h~4 h under −5° C.~40° C., with the mole ratio of NaH and tetraisopropyl methylene diphosphonate being 1:1~3:1;

(2). alkylation reaction:

The compound A comprising substituent of bromine and nitro are added to the reaction liquid resulted from step (1) to perform alkylation reaction under 60° C.~150° C. for 2 h~5 h, the mole ratio of compound A and tetraisopropyl methylene diphosphonate is 1:1~3:1; after reaction organic solvent is added to the reaction liquid for extraction, the organic phase is collected and rotary-dried, and compound I with the methylene substituted by the compound comprising nitro group is obtained;

(3). reduction of nitro:

10% Pd/C catalyst is added to the alcohol solution of compound I obtained in step (2) and hydrogen gas is inlet, reacted under room temperature with 1 to 20 atmospheric pressure for 18 h~48 h, with the weight ratio of compound I and 10% Pd/C catalyst being 1:10~1:5, the solution is filtered and evaporated dried to obtain compound II;

(4). Preparation of diselenium/disulfide compound:

The alkaline solution of Se/S ion is reacted with diazonium salt solution under 60° C.~100° C. for 2 h~8 h, pH of the reaction liquid is adjusted with acid to less than 5, and the precipitate is filtered, and the filtration residue is washed with water, alkaline solution is added to dissolve the precipitate, and filtered, the filtrate is acidized to pH less than 5 and the precipitate is obtained, collected and dried under 80° C.~150° C. to obtain diselenium/disulfide compound (compound III);

(4). cyclization:

Alkaline solution is added to the compound II obtained in step (3) under the temperature of −20° C.~5° C., the pH is adjusted to 7~14, and then the organic solvent of o-seleniumchloroylbenzoyl chloride or o-sulfachloroylbenzoyl chloride is added, and reacted under room temperature for 3 h~8 h, with the mole ratio of compound II and o-seleniumchloroylbenzoyl chloride or o-sulfachloroylbenzoyl chloride being 1:1~1:5, the reaction solution is filtered, and the precipitate is collected and washed with organic solvent, and dried under 60° C.~100° C. for 4 h~24 h to obtain compound V;

(5). hydrolysis:

Alcohol and concentrated hydrochloric acid are added to the compound V obtained in step (4), with 1 g compound V added 5 mL~50 mL alcohol solution and 5 mL~60 mL concentrated hydrochloric acid, refluxed under 90° C.~120° C. for 4 h~10 h, the solvent is removed through reduced pressure distillation, the residue is washed with alcohol, and the solid is vacuum-dried under 50° C.~120° C. for 4 h~10 h, to obtain the diphosphonate compound having formula II.

In the method for preparing the diphosphonate compound having the formula II, the organic solvent in step (2) may be methylene dichloride, methenyl chloride, ethyl acetate or petroleum ether.

In the method for preparing the diphosphonate compound having the formula II, the alkaline solution in step (4) is $NaHCO_3$ solution.

In the method for preparing the diphosphonate compound having the formula II, the organic solvent of o-seleniumchloroylbenzoyl chloride or o-sulfachloroylbenzoyl chloride in step (4) is ethyl ether, methylene dichloride, methenyl chloride or ethyl acetate.

In the method for preparing the diphosphonate compound having the formula II, the o-seleniumchloroylbenzoyl chloride or o-sulfachloroylbenzoyl chloride in step (4) is prepared from the following method:

a. The alkaline solution of Se/S ion is reacted with diazonium salt solution under 60° C.~100° C. for 2 h~8 h, pH of the reaction liquid is adjusted with acid to less than 5, the precipitate is filtered, and the filtration residue is washed with water, basic $NaHCO_3$ solution is added to dissolve the precipitate, and filtered, the filtrate is adjusted to pH less than 5, the precipitate is collected and dried under 80° C.~150° C. to obtain diselenium/disulfide compound;

b. the diselenium/disulfide compound obtained in step a is added into $SOCl_2$, refluxed under 60° C.~90° C. for 2 h~5 h, the solvent is recovered through reduced pressure distillation, with the mole ratio of diselenium/disulfide compound and $SOCl_2$ being 1:2~1:50; petroleum ether is added to the residue, and refluxed under 30° C.~90° C. for 2 h~4 h, and filtered when hot, the filtrate is put still in room temperature for 8 h~24 h, the solid precipitated is dried under 20° C.~50° C. for 12 h~48 h, to obtain o-seleniumchloroylbenzoyl chloride or o-sulfachloroylbenzoyl chloride;

The alkaline solution of Se/S ion is obtained from the reaction of selenium powder or sulfur powder with potassium borohydride and NaOH in water for 3 h~10 h, wherein the mole ratio of potassium borohydride, NaOH and selenium powder/sulfur powder is 1:10~5:1;

The diazonium salt solution is obtained from the reaction of the hydrochloric acid solution of anthranilic acid containing substituent, anthranilate cyclohexane containing substituent or β-alanine containing substituent with $NaNO_2$ solution under room temperature for −20° C.~5° C.; the mole ratio of $NaNO_2$ and anthranilic acid containing substituent, anthranilate cyclohexane containing substituent or β-alanine containing substituent is 1:1~3:1.

The alkaline solution of Se/S ion is obtained from the reaction of selenium powder or sulfur powder with potassium borohydride and NaOH in water for 3 h~10 h, wherein the mole ratio of potassium borohydride, NaOH and selenium powder/sulfur powder is 1:10~5:1;

The diazonium salt solution is obtained from the reaction of the hydrochloric acid solution of anthranilic acid containing substituent, anthranilate cyclohexane containing substituent or β-alanine containing substituent (compound C) with $NaNO_2$ solution under −20° C.~5° C.; the mole ratio of $NaNO_2$ and compound C is 1:1~3:1.

According to the above preparing method, the diphosphonate compound having formula II with $R_1$ being H may be prepared. The above preparing method comprises the following steps:

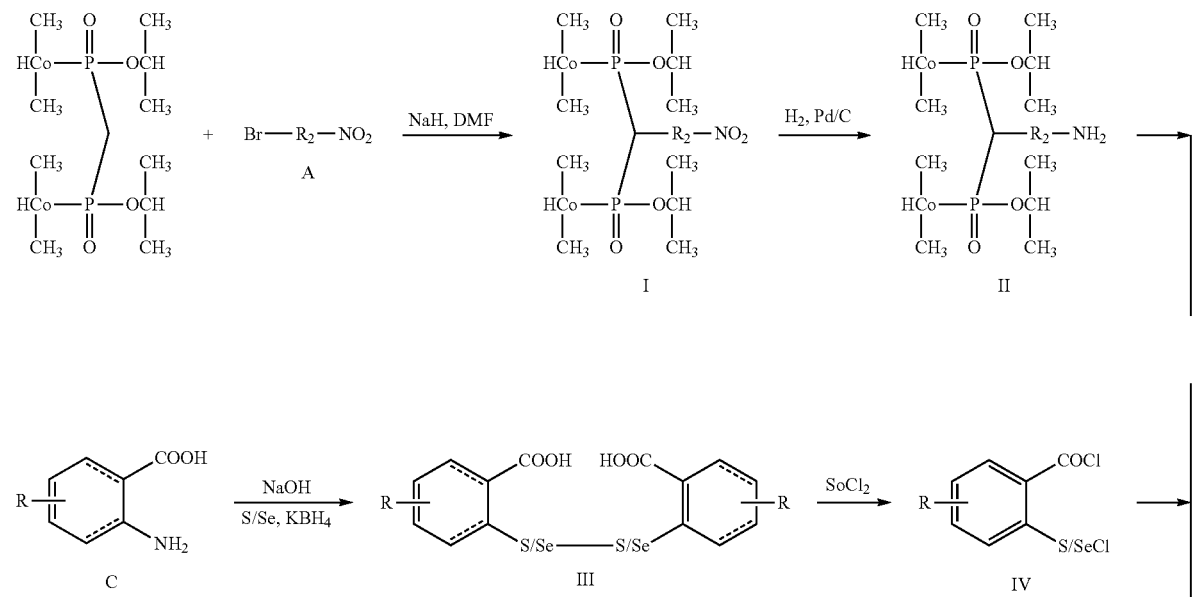

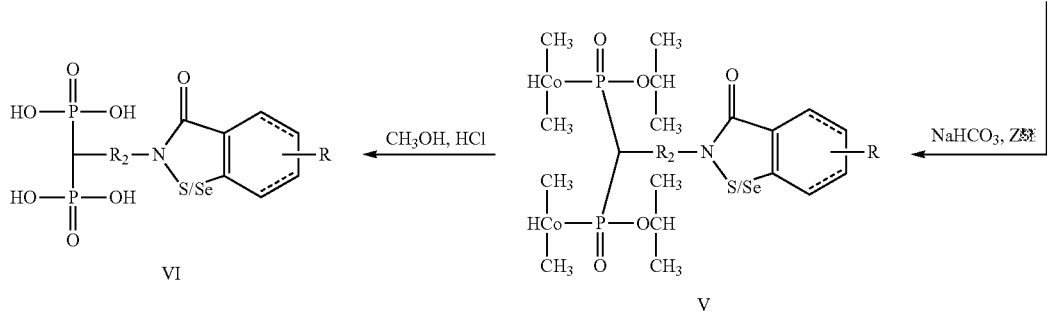

Another method for preparing the above diphosphonate compound having formula II comprises the following steps:

(1). cyclization:

the organic solvent of o-seleniumchloroylbenzoyl chloride or o-sulfachloroylbenzoyl chloride is added into pH 7~14 ω-amino acid methyl ester (compound B), reacted under room temperature for 3 h~8 h, with the mole ratio of o-seleniumchloroylbenzoyl chloride or o-sulfachloroylbenzoyl chloride and compound B being 1:1~3:1, the reaction liquid is filtered, and the precipitate is washed with ethyl ether, and dried under 50° C.~100° C. for 4 h~24 h, to obtain compound VII;

(2). hydrolysis:

Alcohol and concentrated hydrochloric acid is added to the compound VII obtained in step (1), with 1 g compound VII added 2 mL~50 mL alcohol and 5 mL~50 mL concentrated hydrochloric acid, and refluxed under 90° C.~120° C. for 4 h~10 h, the solvent is removed through reduced pressure distillation, the residue is recrystallized with alcohol, to obtain the compound VIII;

(3). phosphoration:

The compound VIII obtained in step (2) is reacted with phosphorous acid and phosphorus trichloride under 90° C.~120° C. for 2 h~6 h, water is added into the reactant, with 1 g compound VIII added 1 mL~50 mL water, refluxed under 90° C.~110° C. for 1 h~3 h, with the mole ratio of compound VIII and phosphorous acid being 1:1~1:5, and the mole ratio of compound VIII and phosphorus trichloride being 1:2~1:6, and the reaction liquid is filtered, alcohol solution is added into the filtrate and put still under −5° C.~5° C. for 12 h~48 h, suction-filtered, and the solid is washed with 5° C.~15° C. cold water, vacuum-dried under 50° C.~120° C. for 4 h~10 h, to obtain the diphosphonate compound (compound IX) having formula II.

In the method for preparing the diphosphonate compound having the formula II, the organic solvent in step (1) may be ethyl ether, methylene dichloride, methenyl chloride or ethyl acetate.

In the method for preparing the diphosphonate compound having the formula II, the method for preparing o-seleniumchloroylbenzoyl chloride or o-sulfachloroylbenzoyl chloride in step (4) is described as above.

According to the above preparing method, the diphosphonate compound having formula II with $R_1$ being OH may be prepared. The above preparing method comprises the following steps:

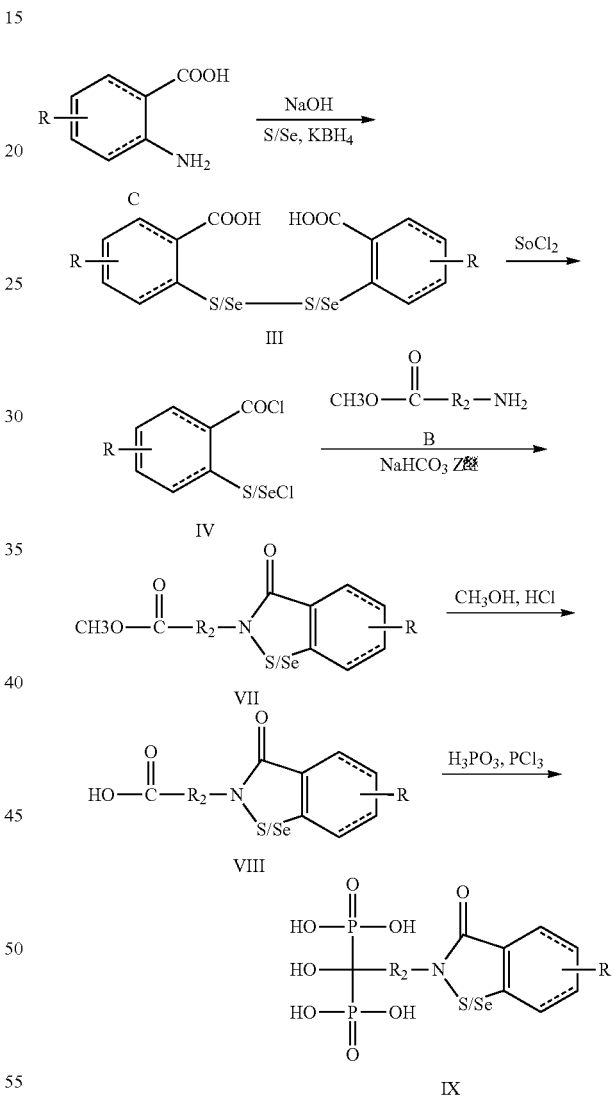

Existing nitrogen-containing diphosphonate are the most widely used drug for treating osteoporosis, such as commercially available Alendronate and Zoledronate, which mainly inhibit the farnesyl diphosphate synthase and therefore reduce the protein level in osteoclast, thus inhibiting the activity of osteoclast and treating osteoporosis. Although the activity of existing nitrogen-containing diphosphonate and its salt becomes higher, i.e. the effect of these compounds on inhibiting osteoclast become stronger, the effect on osteoblast proliferation is weak, which may increase the risk of fracture.

The present invention provides a new diphosphonate compound and a method for preparing the same and an application of the same, and moreover the structural features of the compound are identified. In cellular pharmacodynamics experiments, alendronate sodium commercially available and widely used is taken as positive control, and the results indicate that the new diphosphonate compound provided in the present invention exhibits an activity in inhibiting osteoclast equivalent to alendronate sodium, and a higher activity in affecting the proliferation of osteoplast than the positive control compounds, but the positive control exhibits a weaker effect on osteoplast proliferation. In experimental examples, an administration schedule for the diphosphonate compound of the present invention is provided.

DESCRIPTION OF EMBODIMENTS

In the embodiments exemplified in the present invention, the diphosphonate compound having formula II:

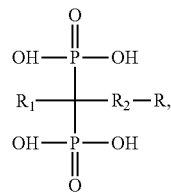

II wherein R is

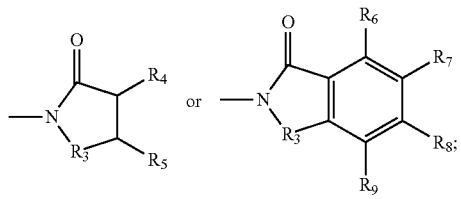

wherein $R_1$ is H, OH or halogen, preferably H, OH; $R_2$ is

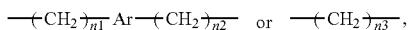

wherein $n_1=1\sim10$, $n_2=0\sim10$, $n_3=1\sim10$, i preferably $n_1=1\sim4$, $n_2=0\sim1$, $n_3=1\sim5$; if $n_1$, $n_2$ or $n_3\geq1$, the alkyl may be substituted by halogen, —CN, —NO$_2$ or —OH; Ar is aryl or substituted aryl, the substituent is C1~C6 alkyl, C1~C6 substituted alkyl, halogen, —CN, —NO$_2$ or —OH, Ar is preferably aryl, more preferably phenyl;

$R_3$ is Se or S, preferably Se;

$R_6$, $R_7$, $R_8$ and $R_9$ are each independently selected from the group consisting of Hydrogen, halogen, —CN, —NO$_2$ or —OH alkyl.

$R_4$ and $R_5$ are independently selected from the group consisting of Hydrogen, halogen, —CN, —NO$_2$, —OH, —OR', —COOR', —OCOOR', —COR', —CON(R')$_2$, —OCON(R')$_2$, —SR, —SO$_2$R, —SO$_2$N(R')$_2$, —SOR' group, C1~C10 alkyl, C1~C10 substituted alkyl, alkenyl, substituted alkenyl, alkynyl, substituted alkynyl aryl or substituted aryl, wherein each of R and RI's independently selected from the group consisting of H, alkyl, aryl, substituted alkyl or substituted aryl; $R_4$ and $R_5$ may also constitute 3~7 carbons of cyclo alkane, the cyclo alkane may be substituted by C1~C6 alkyl, C1~C6 substituted alkyl, halogen, —CN, —NO$_2$ or —OH; $R_4$ and $R_5$ are preferably hydrogen, halogen, —CN, —NO$_2$, —OH;

$R_6$, $R_7$, $R_8$ and $R_9$ are independently selected from the group consisting of Hydrogen, halogen, —CN, —NO$_2$, —OH, —OR', —COOR', —OCOOR', —COR', —CON(R')$_2$, —OCON(R')$_2$, —SR, —SO$_2$R, —SO$_2$N(R')$_2$, —SOR' group, alkyl, alkenyl, alkynyl, aryl, substituted alkyl, substituted alkenyl, substituted alkynyl or substituted aryl, wherein each of R and RI's independently selected from the group consisting of H, alkyl, aryl, substituted alkyl or substituted aryl; $R_6$, $R_7$, $R_8$ and $R_9$ are preferably hydrogen.

That is to say in the embodiments exemplified in the present invention, some diphosphonate compounds have the structure of formula III, other diphosphonate compounds have the structure of formula IV:

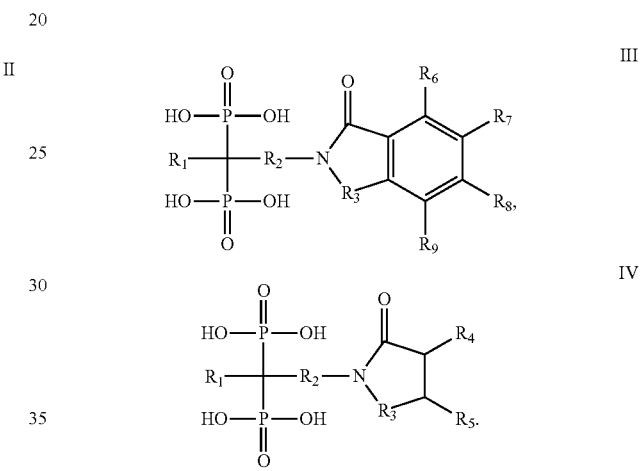

When R1 in the exemplified diphosphonate compound is H, it may be prepared by the method below:

(1). Proton activation of methylene:

Tetraisopropyl methylene diphosphonate and NaH are performed with the proton activation reaction of methylene for 1 h~4 h under −5° C.~40° C., with the mole ratio of NaH and tetraisopropyl methylene diphosphonate being 1:1~3:1;

(2). alkylation reaction:

The compound A substituted by bromine and nitro is added to the reaction liquid resulted from step (1) to perform alkylation reaction under 60° C.~150° C. for 2 h~5 h, the mole ratio of compound A and tetraisopropyl methylene diphosphonate is 1:1~3:1; after reaction organic solvent is added to the reaction liquid for extraction, the organic phase is collected and rotary-dried, to obtain compound I with the methylene substituted by the compound comprising nitro group;

(3). reduction of nitro:

10% Pd/C catalyst is added to the alcohol solution of compound I obtained in step (2) and hydrogen gas is inlet, and reacted under room temperature with 1 to 20 atmospheric pressure for 18 h~48 h, with the weight ratio of compound I and 10% Pd/C catalyst being 1:0.5~1:5, and then filtered and evaporated dry to obtain compound II;

(4). Preparation of diselenium/disulfide compound:

The alkaline solution of Se/S ion is reacted with diazonium salt solution under 60° C.~100° C. for 2 h~8 h, pH of the reaction liquid is adjusted with acid to less than 5, the precipitate is filtered, and the filtration residue is washed with water, alkaline solution is added to dissolve the precipitate, and then the solution is filtered, the filtrate is acidized to pH less than 5, the precipitate is obtained, collected and the precipitate is dried under 80° C.~150° C. to obtain diselenium/disulfide compound (compound III);

(4). cyclization:

Alkaline solution is added to the compound II obtained in step (3) under the temperature of −20° C.~5° C., the pH is adjusted to 7~14, and then the organic solvent of o-seleniumchloroylbenzoyl chloride or o-sulfachloroylbenzoyl chloride is added, and reacted under room temperature for 3 h~8 h, with the mole ratio of compound II and o-seleniumchloroylbenzoyl chloride or o-sulfachloroylbenzoyl chloride being 1:1~1:5, the reaction solution is filtered, and the precipitate is collected and washed with organic solvent, and dried under 60° C.~100° C. for 4 h~24 h, to obtain compound V;

(5). hydrolysis:

Alcohol and concentrated hydrochloric acid are added to the compound V obtained in step (4), with 1 g compound V added 5 mL~50 mL alcohol solution and 5 mL~60 mL concentrated hydrochloric acid, and refluxed under 90° C.~120° C. for 4 h~10 h, the solvent is removed through reduced pressure distillation, and the residue is washed with alcohol, and the solid obtained is vacuum-dried under 50° C.~120° C. for 4 h~10 h, to obtain the diphosphonate compound having formula II.

The organic solvent in step (2) may be methylene dichloride, methenyl chloride, ethyl acetate or petroleum ether.

The alkaline solution in step (4) is $NaHCO_3$ solution, the organic solvent of o-seleniumchloroylbenzoyl chloride or o-sulfachloroylbenzoyl chloride is ethyl ether, methylene dichloride, methenyl chloride, ethyl acetate.

The o-seleniumchloroylbenzoyl chloride or o-sulfachloroylbenzoyl chloride in step (4) is prepared from the following method:

a. The alkaline solution of Se/S ion is reacted with diazonium salt solution under 60° C.~100° C. for 2 h~8 h, pH of the reaction liquid is adjusted with acid to less than 5, and the precipitate is filtered, the filtration residue is washed with water, basic $NaHCO_3$ solution is added to dissolve the precipitate, and then the solution is filtered, the filtrate is acidized to pH less than 5, the precipitate is collected and dried under 80° C.~150° C. to obtain diselenium/disulfide compound;

b. The diselenium/disulfide compound obtained in step a is added into $SOCl_2$, and refluxed under 60° C.~90° C. for 2 h~5 h, the solvent is recovered through reduced pressure distillation, with the mole ratio of diselenium/disulfide compound and $SOCl_2$ being 1:2~1:50; petroleum ether is added to the residue, and refluxed under 30° C.~90° C. for 2 h~4 h, filtered when hot, the filtrate is put still in room temperature for 8 h~24 h, the solid precipitated is dried under 0° C.~50° C. for 12 h~48 h, to obtain o-seleniumchloroylbenzoyl chloride or o-sulfachloroylbenzoyl chloride;

The alkaline solution of Se/S ion is obtained from the reaction of selenium powder or sulfur powder with potassium borohydride and NaOH in water for 3 h~10 h, wherein the mole ratio of potassium borohydride, NaOH and selenium powder/sulfur powder is 1:10~5:1;

The diazonium salt solution is obtained from the reaction of the hydrochloric acid solution of anthranilic acid containing substituent, anthranilate cyclohexane containing substituent or β-alanine containing substituent with $NaNO_2$ solution under room temperature for −20° C.~5° C.; the mole ratio of $NaNO_2$ and anthranilic acid containing substituent, anthranilate cyclohexane containing substituent or β-alanine containing substituent is 1:1-3:1.

The alkaline solution of Se/S ion is obtained from the reaction of selenium powder or sulfur powder with potassium borohydride and NaOH in water for 3 h~10 h, wherein the mole ratio of potassium borohydride, NaOH and selenium powder/sulfur powder is 1:10~5:1;

The diazonium salt solution is obtained from the reaction of the hydrochloric acid solution of anthranilic acid containing substituent, anthranilate cyclohexane containing substituent or β-alanine containing substituent (compound C) with $NaNO_2$ solution under −20° C.~5° C.; the mole ratio of $NaNO_2$ and compound C is 1:1~3:1.

When $R_1$ in the exemplified diphosphonate compound is OH, it may be prepared by the method below:

(1). cyclization:

The organic solvent of o-seleniumchloroylbenzoyl chloride or o-sulfachloroylbenzoyl chloride is added into pH 7~14 ω-amino acid methyl ester (compound B), and reacted under room temperature for 3 h~8 h, with the mole ratio of o-seleniumchloroylbenzoyl chloride or o-sulfachloroylbenzoyl chloride and compound B being 1~3:1, the reaction liquid is filtered, and the precipitate is washed with ethyl ether, and dried under 50° C.~100° C. for 4 h~24 h, to obtain compound VII;

(2). hydrolysis:

Alcohol and concentrated hydrochloric acid are added to the compound VII obtained in step (1), with 1 g compound VII added 2 mL~50 mL alcohol and 5 mL~50 mL concentrated hydrochloric acid, and refluxed under 90° C.~120° C. for 4 h~10 h, the solvent is removed through reduced pressure distillation, the residue is recrystallized with alcohol, to obtain the compound VIII;

(3). phosphoration:

The compound VIII obtained in step (2) is reacted with phosphorous acid and phosphorus trichloride under 90° C.~120° C. for 2 h~6 h, water is added into the reactant, with 1 g compound VIII added 1 mL~50 mL water, and refluxed under 90° C.~110° C. for 1 h~3 h, with the mole ratio of compound VIII and phosphorous acid being 1:1~1:5, and the mole ratio of compound VIII and phosphorus trichloride being 1:2~1:6, the reaction liquid is filtered, alcohol solution is added into the filtrate and put still under −5° C.~50° C. for 12 h~48 h, and suction-filtered, and the solid is washed with 5° C.~15° C. cold water, and vacuum-dried under 50° C.~120° C. for 4 h~10 h, to obtain the diphosphonate compound (compound IX) having formula II.

The organic solvent in step (1) may be ethyl ether, methylene dichloride, methenyl chloride or ethyl acetate.

The method for preparing o-seleniumchloroylbenzoyl chloride or o-sulfachloroylbenzoyl chloride in step (4) is described as above.

The present invention will be further described in connection with the particular embodiments. But it should be understood that the scope of the present invention is not limited to the particular embodiments, the achieved technologies based on the content of the present invention fall in the scope of the present invention.

Example 1

SC-1

The diphosphonate compound in this embodiment is 4-(3-carbonylbenzo[d][1,2]selenazole-2(3H))-benzyl-methylene diphosphonic acid, having the following formula:

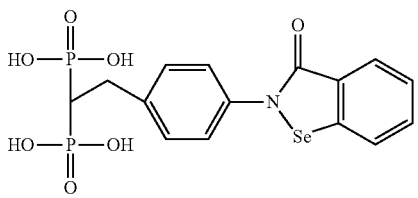

The method for preparing the compound comprises the following steps:

50 mL aqueous solution of 12 g KBH$_4$ is slowly added dropwise to 400 mL aqueous solution of 64 g selenium powder in room temperature, and then 64 g selenium powder is added, and stirred in room temperature for 2 h, and then 75 mL 9 mol/L NaOH solution is added, and stirred for 3 h to obtain the alkaline solution of Se ion.

240 g o-aminobenzoic acid is added into 500 mL water and 400 mL concentrated HCl, completely dissolved, and put still in 0° C.~5° C. ice water bath. 12 g NaNO$_2$ is added into 50 mL water and stirred to dissolve, and then added dropwise into o-aminobenzoic acid solution, and the temperature is controlled between 0° C.~5° C., Potassium iodide-starch test paper is used to determine the end of reaction (drip one drop of reaction liquid onto potassium iodide-starch test paper, the test paper turning blue indicates complete reaction) to obtain diazonium salt solution.

The diazonium salt solution is added dropwise to the prepared alkaline solution of Se ion, after dripping, the temperature is raised to 60° C., reacted for 5 h. pH of the reaction liquid is adjusted with concentrated hydrochloric acid to less than 3, and yellow precipitate is obtained, filtered and washed with water. Then NaHCO$_3$ is added, dissolved, boiled and filtered, and the filtrate is acidized by diluted hydrochloric acid and pH is adjusted to less than 3, and yellow precipitate is obtained, filtered and white-like or light yellow filter cake is obtained, and dried under 100° C. to obtain benzoic acid 2,2'-diselenide.

150 g benzoic acid 2,2'-diselenide is added to 650 mL SOCl$_2$ solution, refluxed under 80° C. for 3 h, and the solvent is removed through reduced pressure distillation, and the residue is added to 400 mL petroleum ether, heated up and refluxed for 30 min. The reaction liquid is filtered when hot, and the filtrate is put still in room temperature to crystallize, and yellow solid is obtained, and filtered, and the filter cake is dried in room temperature with good ventilation and 2-o-seleniumchloroylbenzoyl chloride is obtained.

206 g tetraisopropyl methylene diphosphonate is added dropwise to 600 mL DMF of 25.2 g sodium hydride and stirred, and reacted under room temperature for 2 h. 156 g 4-nitrobenzyl bromide is added, and heated up to 80° C. and reacted for 4 h, after reaction 250 mL ethyl acetate is added to the reaction liquid to extract, and the organic phase is collected and rotary-dried to obtain tetraisopropyl 4-nitrobenzyl methylene diphosphonate.

50 g tetraisopropyl 4-nitrobenzyl methylene diphosphonate is dissolved in 500 mL methanol and 30 g 10% Pd—C is added, and the hydrogen is inlet for 24 h reduction reaction, and the filtrate is collected and rotary-dried to obtain tetraisopropyl 4-amino benzylmethylene diphosphonate.

The ethyl ether solution of 30 g 2-o-seleniumchloroylbenzoyl chloride is added dropwise to the mixed liquid of 50 g tetraisopropyl 4-amino benzylmethylene diphosphonate, 40 g sodium bicarbonate and 400 mL water and stirred, and the reaction liquid is cooled in ice bath, and reacted in ice-water bath for 2 h and reacted in room temperature for 4 h. The reaction liquid is filtered and the filter cake is washed with ethyl ether and dried under 60° C. for 8 h to obtain 4-(3-carbonylbenzo[d][1,2]selenazole-2(3H))-tetraisopropyl benzyl-methylene diphosphonate.

800 mL methanol and 1600 mL concentrated hydrochloric acid are added to 40 g 4-(3-carbonylbenzo[d][1,2]selenazole-2(3H))-tetraisopropylbenzyl-methylene diphosphonate, and refluxed under 110° C. for 6 h. The reaction liquid is filtered after reaction, and the filtrate is evaporated and dried, and the residue is washed with methanol and dried in 105° C. vacuum drying oven for 10 h to obtain white solid.

Identification of the white solid:

600 MHZ (Advance Bruker) 1H-NMR (DMSO, δ) 2.25~2.39 (t, 1H); 3.05~3.17 (d, 2H); 7.335 (d, 2H); 7.452~7.471 (t, 1H); 7.514~7.535 (d, 2H); 7.651~7.692 (t, 1H); 7.883~7.903 (d, 1H); 8.085~8.105 (d, 1H); 10.330~10.512 (S, 4H).

Finnigan MAT 4510 ESI-MS (Thermo Electron): 462.

Element analysis: Se is 16.9% analyzed by Chinese 2005 edition pharmacopoeia selenium content analysis method, P is 13.5% analyzed by Chinese 2005 edition pharmacopoeia phosphorus content analysis method.

It can be determined from the above identifications that the white solid is 4-(3-carbonylbenzo[d][1,2]selenazole-2(3H))-benzyl-methylene diphosphonic acid.

Example 2

SC-2

The diphosphonate compound in this embodiment is 4-(3-carbonylbenzo[d][1,2]selenazole-2(3H))-benzyl-methylene-1-hydroxyl-methylene diphosphonic acid, having the following formula:

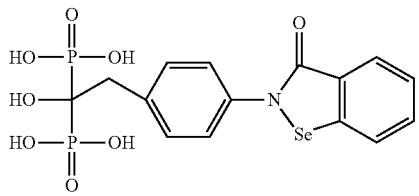

The method for preparing the compound comprises the following steps:

The ethyl ether solution of 80 g 2-o-seleniumchloroylbenzoyl chloride is added dropwise to the mixed liquid of 50 g methyl p-aminobenzenacetate, 15 g sodium bicarbonate and 600 mL water and stirred, and the reaction liquid is cooled in ice bath, and reacted in ice-water bath for 2 h and reacted in room temperature for 4 h. The reaction liquid is filtered and the filter cake is washed with ethyl ether and dried under 60° C. for 8 h to obtain p-(3-carbonylbenzo[d][1,2]selenazole-2(3H))-methyl phenyl acetate.

9 g phosphorous acid is heated up to 100° C. and dissolved, and 50 g p-(3-carbonylbenzo[d][1,2]selenazole-2(3H))-methylphenyl acetate is added, stirred to dissolve, and 26 g phosphorus trichloride is added dropwise, and the agitation is kept for 4 h, 400 mL water is added when the product go stiff, and refluxed under 105° C. for 2 h. The reaction liquid is filtered and the filtrate is added with methanol and put still under 5° C. for 24 h, suction-filtered, and the solid is washed with cold water, and vacuum-dried under 100° C. for 6 h to obtain white solid.

Identification of the white solid:

1H-NMR (DMSO, δ) 3.12~3.25 (S, 2H); 7.336~7.340 (d, 2H); 7.450~7.469 (t, 1H); 7.517~7.537 (d, 2H); 7.650~7.693 (t, 1H); 7.884~7.902 (d, 1H); 8.08~8.100 (d, 1H); 9.456 (S, 1H); 10.347~10.523 (S, 4H).

ESI-MS: 478.

Elemental analysis: Se 16.5%, P 13.0%.

It can be determined from the above identifications that the white solid is 4-(3-carbonylbenzo[d][1,2]selenazole-2(3H))-benzyl-1-hydroxyl-methylenediphosphonic acid.

Example 3

SC-3

The diphosphonate compound in this embodiment is 2-(3-carbonylbenzo[d][1,2]selenazole-2(3H))-ethyl-methylene diphosphonic acid, having the following formula:

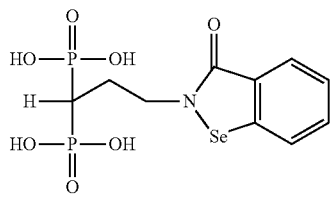 [SMILES: O=c1c2ccccc2[se]n1CCC(P(=O)(O)O)P(=O)(O)O]

The method for preparing the compound comprises the following steps:

200 g tetraisopropyl methylene diphosphonate is added dropwise to 600 mL DMF of 25 g sodium hydride and stirred, and reacted under room temperature for 2 h. 86 g 2-amino ethyl bromide is added to the reaction bulb, after addition the temperature is heated up to 80° C. to react for 4 h, after reaction 250 mL ethyl acetate is added to the reaction liquid to extract, and the organic phase is collected and rotary-dried to obtain tetraisopropyl 2-nitro ethyl methylene diphosphonate.

50 g tetraisopropyl 2-nitroethyl methylene diphosphonate is dissolved in 500 mL methanol, and 20 g 10% Pd—C is added, and the hydrogen is inlet for 24 h reduction reaction, and the filtrate is collected and rotary-dried to obtain tetraisopropyl 2-amino ethyl methylene diphosphonate.

The ethyl ether solution of 30 g 2-benzoyl chloride is added dropwise to the mixed liquid of 50 g tetraisopropyl 2-amino ethyl diphosphonate, 30 g sodium bicarbonate and 350 mL water and stirred, and the reaction liquid is cooled in ice bath, and reacted in ice-water bath for 2 h and reacted in room temperature for 4 h. The reaction liquid is filtered and the filter cake is washed with ethyl ether and dried under 60° C. for 8 h to obtain 2-(3-carbonylbenzo[d][1,2]selenazole-2(3H))-tetraisopropylethyl-methylene diphosphonate.

40 g 2-(3-carbonylbenzo[d][1,2]selenazole-2(3H))-tetraisopropylethyl-methylene diphosphonate is added to 400 mL methanol and 800 mL concentrated hydrochloric acid and refluxed under 110° C. for 6 h. After reaction the reaction liquid is cooled, and filtered, and the filtrate is evaporated and dried, and the residue is washed with methanol and dried in 105° C. vacuum drying oven for 10 h to obtain white solid.

Identification of the white solid:

1H-NMR (DMSO, δ) 1.36~1.52 (t, 1H); 1.54~1.69 (m, 2H); 3.71~3.84 (t, 2H); 7.450~7.474 (t, 1H); 7.652~7.693 (t, 1H); 7.882~7.896 (d, 1H); 8.085~8.111 (d, 1H); 10.325~10.552 (S, 4H).

ESI-MS: 412.

Element analysis: Se 19.2%, P 14.9%.

It is determined that the white solid is 2-(3-carbonylbenzo[d][1,2]selenazole-2(3H))-ethyl-methylene diphosphonic acid.

Example 4

SC-4

The diphosphonate compound in this embodiment is 2-(3-carbonylbenzo[d][1,2]selenazole-2(3H))-ethyl-1-hydroxyl-methylene diphosphonic acid, having the following formula:

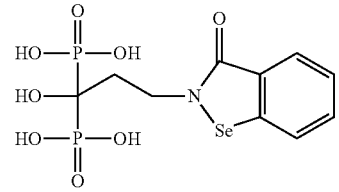 [SMILES: O=c1c2ccccc2[se]n1CCC(O)(P(=O)(O)O)P(=O)(O)O]

The method for preparing the compound comprises the following steps:

The ethyl ether solution of 80 g 2-o-seleniumchloroylbenzoyl chloride is added dropwise to the mixed liquid of 31 g 3-alaninemethyl ester, 8 g sodium bicarbonate and 350 mL water and stirred, and the reaction liquid is cooled in ice bath, and reacted in ice-water bath for 1 h and reacted in room temperature for 3 h. The reaction liquid is filtered and the filter cake is washed with ethyl ether and dried under 60° C. for 8 h to obtain 3-(3-carbonylbenzo[d][1,2]selenazole-2(3H))-methyl propionate.

8 g phosphorous acid is heated up to 100° C. and dissolved, 50 g 3-(3-carbonylbenzo[d][1,2]selenazole-2(3H))-methyl propionate is added, stirred to dissolve, and 30 g phosphorus trichloride is added dropwise, and the agitation is kept for 4 h, 400 mL water is added when the product go stiff, and refluxed under 105° C. for 2 h. The reaction liquid is filtered and the filtrate is added with methanol and put still under 5° C. for 24 h, suction-filtered, and the solid is washed with cold water, and vacuum-dried under 100° C. for 6 h to obtain white solid.

Identification of the white solid:

1H-NMR (DMSO, δ) 1.77~1.94 (m, 2H); 3.69~3.80 (t, 2H); 7.444~7.464 (t, 1H); 7.642~7.687 (t, 1H); 7.889~7.903 (d, 1H); 8.081~8.109 (d, 1H); 9.210 (S, 1H); 10.320~10.502 (S, 4H).

ESI-MS: 428.

Element analysis: Se 18.4%, P 14.5%.

It is determined that the white solid is 2-(3-carbonylbenzo[d][1,2]selenazole-2(3H))-benzyl-1-hydroxyl-methylene diphosphonic acid.

Example 5

SC-5

The diphosphonate compound in this embodiment is 4-(4,5-dimethyl-1,2-seleniumazolidine-3-ketone)-benzyl-methylene diphosphonic acid, having the following formula:

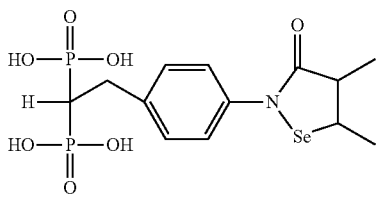 [SMILES: CC1[Se]N(c2ccc(CC(P(=O)(O)O)P(=O)(O)O)cc2)C(=O)C1C]

The method for preparing the compound comprises the following steps:

50 mL aqueous solution of 12 g KBH$_4$ is slowly added dropwise to 400 mL aqueous solution of 64 g selenium powder in room temperature, and then 64 g selenium powder is added, stirred in room temperature for 3 h, and then 80 mL 9 mol/L NaOH solution is added, and the agitation is kept for 3 h to obtain the alkaline solution of Se ion.

205 g 2-methyl β-butyrine is added to 500 mL water and 400 mL concentrated HCl, completely dissolved, and placed in 0~5° C. ice-water bath, and 12 g NaNO$_2$ is added to 50 mL water and stirred to dissolve, and then added dropwise to 2-methyl β-butyrine solution, and the dripping speed is controlled to keep the temperature between 0~5° C., and the potassium iodide-starch test paper is used to determine the end of reaction, and the diazonium salt solution is obtained.

The diazonium salt solution is added dropwise to the above Se ion solution, after dripping, the temperature of the reaction liquid is raised to 60° C., reacted for 5 h. pH of the reaction liquid is adjusted by concentrated hydrochloric acid to less than 3, and the white precipitate is obtained, filtered, and washed with water. NaHCO$_3$ is then added, dissolved and boiled, and then filtered, and the filtrate is acidified with diluted hydrochloric acid, and pH is adjusted to less than 1, and the white precipitate is obtained, filtered, and the white filter cake is obtained, and dried under 100° C. to obtain 3,3'-selenium-2-methyl-butanoic acid.

150 g 3,3'-selenium-2-methyl butanoic acid is added into 400 mL SOCl$_2$ solution, refluxed under 80° C. for 2 h, and the solvent is recovered through reduced pressure distillation, and the residue is added to 300 mL petroleum ether, and heated up and refluxed for 30 min. The reaction liquid is filtered while hot, and the filtrate is put still in room temperature to crystallize in low temperature, and the precipitated solid is filtered, and the filter cake is dried in room temperature with good ventilation, to obtain 3-selenium-2-methylbutyricacidchloride.

The ethyl ether solution of 25 g 3-selenium-2-methyl butyric acid chloride is added dropwise to the mixed liquid of 50 g tetraisopropyl 4-aminobenzyl methylene diphosphonate, 40 g sodium bicarbonate and 400 mL water and stirred, and the reaction liquid is cooled in ice bath, and reacted in ice-water bath for 2 h and reacted in room temperature for 4 h. The reaction liquid is filtered and the filter cake is washed with ethyl ether and dried under 60° C. for 8 h to obtain 4-(4,5-dimethyl-1,2-seleniumazolidine-3-ketone)-tetraisopropylbenzyl-methylene diphosphonate.

40 g 4-(4,5-dimethyl-1,2-seleniumazolidine-3-ketone)-tetraisopropylbenzyl-methylene diphosphonate is added to 500 mL methanol and 1000 mL concentrated hydrochloric acid, and refluxed under 110° C. for 6 h. After reaction the reaction liquid is cooled, and filtered, and the filtrate is evaporated and dried, and the residue is washed with methanol and dried in 105° C. vacuum drying oven for 10 h to obtain light yellow solid.

Identification of the light yellow solid:
1H-NMR (DMSO, δ) 1.40~1.58 (d, 3H); 1.67~1.89 (d, 3H); 2.20~2.34 (m, 1H); 2.36~2.48 (m, 1H); 2.87~2.97 (t, 1H); 3.05~3.17 (d, 2H); 7.334~7.356 (d, 2H); 7.510~7.534 (d, 2H); 10.310~10.576 (S, 4H).
ESI-MS: 440.
Element analysis: Se 7.9%, P 14.1%.
It is determined that the light yellow solid is 4-(4,5-dimethyl-1,2-seleniumazolidine-3-ketone)-benzyl-methylene diphosphonic acid.

Example 6

SC-6

The diphosphonate compound in this embodiment is 4-(4,5-dimethyl-1,2-seleniumazolidine-3-ketone)-benzyl-1-hydroxyl-methylene diphosphonic acid, having the following formula:

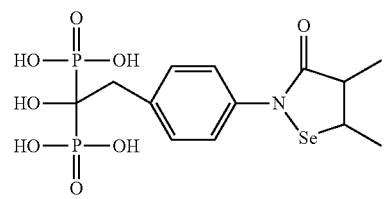 [SMILES: CC1[Se]N(c2ccc(CC(O)(P(=O)(O)O)P(=O)(O)O)cc2)C(=O)C1C]

The method for preparing the compound comprises the following steps:

The ethyl ether solution of 70 g 3-selenium-2-methylbutyryl chloride is added dropwise to the mixed liquid of 50 g methyl-(4-aminophenyl)acetate, 15 g sodium bicarbonate and 600 mL water and stirred, and the reaction liquid is cooled in ice bath, and reacted in ice-water bath for 2 h and reacted in room temperature for 4 h. The reaction liquid is filtered and the filter cake is washed with ethyl ether and dried under 60° C. for 8 h to obtain 4-(4,5-dimethyl-1,2-seleniumazolidine-3-ketone)-methylphenyl acetate.

8.5 g phosphorous acid is heated up to 90° C.~120° C. and dissolved, and 50 g 4-(4,5-dimethyl-1,2-seleniumazolidine-3-ketone)-methylphenyl acetate is added, stirred to dissolve, and 28 g phosphorus trichloride is added dropwise, and the agitation is kept for 4 h, water is added when the product go stiff, and refluxed under 105° C. for 2 h. The reaction liquid is filtered and the filtrate is added with methanol and put still under 5° C. for 17 h, suction-filtered, and the solid is washed with cold water, and vacuum-dried under 100° C. for 6 h, to obtain white solid.

Identification of the white solid:
1H-NMR (DMSO, δ) 1.38~1.49 (d, 3H); 1.65~1.79 (d, 3H); 2.23~2.34 (m, 1H); 2.83~2.95 (m, 2H); 3.03~3.18 (S, 2H); 7.336~7.356 (d, 2H); 7.509~7.531 (d, 2H); 9.450 S, 1H); 10.309~10.594 (S, 4H).
ESI-MS: 456.
Element analysis: Se 17.2%, P 13.7%.
It is determined that the light yellow solid is 4-(4,5-dimethyl-1,2-seleniumazolidine-3-ketone)-benzyl-1-hydroxyl-methylene diphosphonic acid.

Example 7

SC-7

The diphosphonate compound in this embodiment is 4-(3-carbonylcyclohexano[d][1,2]selenazole-2(3H))-benzyl-methylene-diphosphonic acid, having the following formula:

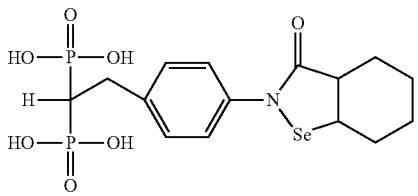 [SMILES: O=C1C2CCCCC2[Se]N1c1ccc(CC(P(=O)(O)O)P(=O)(O)O)cc1]

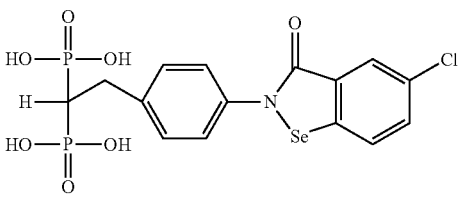

The diphosphonic acid compound is prepared from the same synthesis process with embodiment 5, but the only difference is that 2-amino cyclohexane carboxylic acid replaces 2-methyl-β butyrine to obtain white solid.

Identification of the white solid:

1H-NMR (DMSO, δ) 1.39~1.49 (m, 4H); 1.50~1.59 (m, 2H); 1.65~1.90 (m, 2H); 2.01~2.19 (m, 1H); 2.25~2.39 (t, 1H); 2.71~2.93 (m, 1H); 3.05~3.17 (d, 2H); 7.307~7.331 (d, 2H); 7.519~7.546 (d, 2H); 10.219~10.491 (S, 4H).

ESI-MS: 466.

Element analysis: Se 17.1%, P 13.2%.

It is determined that the white solid is 4-(3-carbonylcyclohexano[d][1,2]selenazole-2(3H))-benzyl-methylene diphosphonic acid.

The diphosphonic acid compound is prepared from the same synthesis process with embodiment 1, but the only difference is that anthranilic acid is replaced by 2-amino-5-chlorine-benzoic acid to obtain white-like solid 4-(3-carbonyl-5-chlorobenzo[d][1,2]selenazole-2(3H))-benzyl-methylene diphosphonic acid.

1H-NMR (DMSO, δ) 2.20~2.47 (t, 1H); 3.03~3.21 (d, 2H); 7.331~7.356 (d, 2H); 7.447~7.476 (d, 1H); 7.510~7.536 (d, 2H); 7.880~7.911 (d, 1H); 8.193~8.203 (s, 1H); 10.331~10.489 S, 4H).

ESI-MS: 496

Element analysis: Se 15.8%, P 12.6%

It is determined that the white solid is 4-(3-carbonyl-5-cyclohexano[d][1,2]selenazole-2(3H))-benzyl-methylene diphosphonic acid.

Example 8

SC-8

The diphosphonate compound in this embodiment is 4-(3-carbonylcyclohexano[d][1,2]selenazole-2(3H))-benzyl-1-hydroxyl-methylenediphosphonic acid, having the following formula:

Example 10

SC-10

The diphosphonate compound in this embodiment is 4-(3-carbonyl-5-chlorobenzo[d][1,2]selenazole-2(3H))-benzyl-1-hydroxyl-methylene diphosphonic acid, having the following formula:

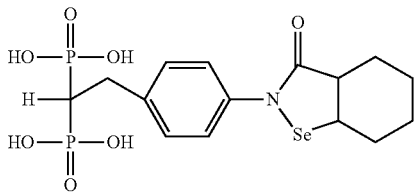 [SMILES: O=C1C2CCCCC2[Se]N1c1ccc(CC(P(=O)(O)O)P(=O)(O)O)cc1]

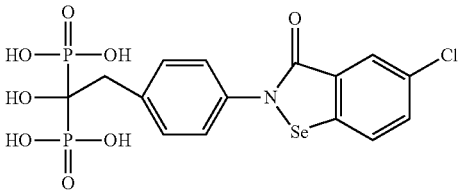 [SMILES: O=c1c2cc(Cl)ccc2[se]n1-c1ccc(CC(O)(P(=O)(O)O)P(=O)(O)O)cc1]

The diphosphonic acid compound is prepared from the same synthesis process with embodiment 6, but the only difference is that 2-methyl-β-butyrine is replaced by 2-aminocyclohexanecarboxylic acid to obtain white solid.

Identification of the white solid:

1H-NMR (DMSO, δ) 1.29~1.38 (m, 4H); 1.42~1.58 (m, 2H); 1.61~1.87 (m, 2H); 2.02~2.21 (m, 1H); 2.68~2.93 (m, 1H); 3.20~3.42 (s, 2H); 7.311~7.33 (d, 2H); 7.511~7.536 (d, 2H); 9.347 S, 1H); 10.301~10.485 (S, 4H).

ESI-MS: 482;

Element analysis: Se 16.3%, P 12.9%.

It is determined that the white solid is 4-(3-carbonylcyclohexano[d][1,2]selenazole-2(3H))-benzyl-1-hydroxyl-methylene diphosphonic acid.

Example 9

SC-9

The diphosphonate compound in this embodiment is 4-(3-carbonyl-5-chlorobenzo[d][1,2]selenazole-2(3H))-benzyl-methylene diphosphonic acid, having the following formula:

The diphosphonic acid compound is prepared from the same synthesis process with embodiment 2, but the only difference is that anthranilic acid is replaced by 2-amino-5-chlorine-benzoic acid to obtain white-like solid.

1H-NMR (DMSO, δ) 3.21~3.39 (S, 2H); 7.330~7.351 (d, 2H); 7.447~7.473 (d, 1H); 7.511~7.536 (d, 2H); 7.877~7.903 (d, 1H); 8.190~8.213 (s, 1H); 9.447 (S, 1H); 10.278~10.504 (S, 4H).

ESI-MS: 512.

Element analysis: Se 15.6%, P 12.0%.

It is determined that the white solid is 4-(3-carbonyl-5-cyclohexano[d][1,2]selenazole-2(3H))-benzyl-1-hydroxyl-methylene diphosphonic acid.

Example 11

SC-11

The diphosphonate compound in this embodiment is 4-(2-methylbenzo[d][1,2]selenazole-3 (2H)-ketone)-benzyl-methylene diphosphonic acid, having the following formula:

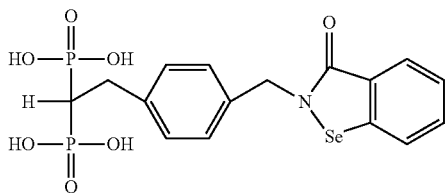 [SMILES: O=c1c2ccccc2[se]n1Cc1ccc(CC(P(=O)(O)O)P(=O)(O)O)cc1]

The diphosphonic acid compound is prepared from the same synthesis process with embodiment 1, but the only difference is that 4-nitrobenzyl bromide is replaced by 4-nitromethylbenzyl bromide to obtain white solid.

1H-NMR (DMSO, δ) 2.20~2.41 (t, 1H); 3.05~3.19 (d, 2H); 5.171~5.192 (S, 2H); 7.316~7.334 (d, 2H); 7.450~7.470 (t, 1H); 7.512~7.530 (d, 2H); 7.650~7.694 (t, 1H); 7.879~7.896 (d, 1H); 8.089~8.112 (d, 1H); 10.321~10.507 (S, 4H).

ESI-MS: 476.

Element analysis: Se 16.7%, P 13.1%.

It is determined that the white solid is 4-(2-methylbenzo[d][1,2]selenazole-3 (2H)-ketone)-benzyl-methylene diphosphonic acid.

Example 12

SC-12

The diphosphonate compound in this embodiment is 4-(2-methylbenzo[d][1,2]selenazole-3 (2H)-ketone)-benzyl-1-hydroxyl-methylene diphosphonic acid, having the following formula:

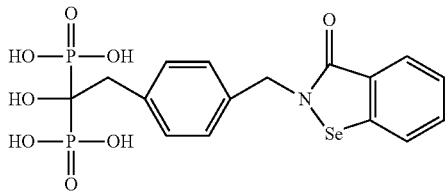 [SMILES: O=c1c2ccccc2[se]n1Cc1ccc(CC(O)(P(=O)(O)O)P(=O)(O)O)cc1]

The diphosphonic acid compound is prepared from the same synthesis process with embodiment 2, but the only difference is that methyl-(4-aminophenyl)acetate is replaced by methyl-a-methyl-p-amino phenyl acetate to obtain white solid.

1H-NMR (DMSO, δ) 3.12~3.27 (S, 2H); 5.170~5.191 (S, 2H); 7.319~7.331 (d, 2H); 7.450~7.471 (t, 1H); 7.510~7.530 (d, 2H); 7.643~7.690 (t, 1H); 7.880~7.901 (d, 1H); 8.083~8.115 (d, 1H); 9.468 S, 1H); 10.320~10.511 (S, 4H).

ESI-MS: 492.

Element analysis: Se 15.9%, P 12.5%.

It is determined that the white solid is 4-(2-methylbenzo[d][1,2]selenazole-3 (2H)-ketone)-benzyl-1-hydroxyl-methylene diphosphonic acid.

Example 13

SC-13

The diphosphonate compound in this embodiment is 4-(3-carbonylbenzo[d][1,2]selenazole-2(3H))-phenylethyl-methylenediphosphonic acid, having the following formula:

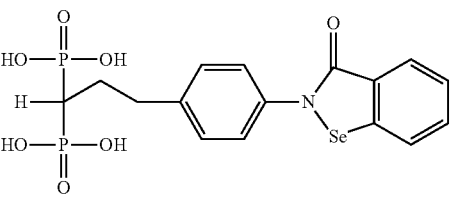 [SMILES: O=c1c2ccccc2[se]n1-c1ccc(CCC(O)(P(=O)(O)O)P(=O)(O)O)cc1]

The diphosphonic acid compound is prepared from the same synthesis process with example 1, but the only difference is that 4-nitrobenzyl bromide is replaced by 4-nitro-(2-bromomethyl)-benzene to obtain light yellow solid.

1H-NMR (DMSO, δ) 1.35~1.49 (t, 1H); 1.65~1.79 (m, 2H); 3.00~3.12 (t, 2H); 7.336~7.41 (d, 2H); 7.453~7.475 (t, 1H); 7.510~7.534 (d, 2H); 7.651~7.693 (t, 1H); 7.882~7.900 (d, 1H); 8.088~8.115 (d, 1H); 10.329~10.515 (S, 4H).

ESI-MS: 476.

Element analysis: Se 16.6%, P 13.2%.

It is determined that the white solid is 4-(3-carbonylbenzo[d][1,2]selenazole-2(3H))-phenylethyl-methylene diphosphonic acid.

Example 14

SC-14

The diphosphonate compound in this embodiment is 4-(3-carbonylbenzo[d][1,2]selenazole-2(3H))-phenylethyl-1-hydroxyl-methylene diphosphonic acid, having the following formula:

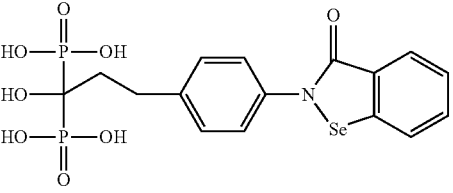

The diphosphonic acid compound is prepared from the same synthesis process with embodiment 2, but the only difference is that methyl 4-amino phenyl acetate is replaced by methyl 4-nitro-phenylpropionatere to obtain white solid.

1H-NMR (DMSO, δ) 1.52~1.83 (t, 2H); 3.01~3.10 (t, 2H); 7.334~7.42 (d, 2H); 7.455~7.477 (t, 1H); 7.510~7.532 (d, 2H); 7.652~7.693 (t, 1H); 7.882~7.901 (d, 1H); 8.083~8.112 (d, 1H); 9.378 (S, 1H); 10.329~10.512 (S, 4H).

ESI-MS: 492.

Element analysis: Se 16.2%, P 12.5%.

It is determined that the white solid is 4-(3-carbonylbenzo[d][1,2]selenazole-2(3H))-phenylethyl-1-hydroxyl-methylene diphosphonic acid Example 15

SC-15

The diphosphonate compound in this embodiment is 4-(3-carbonylbenzo[d][1,2]sulfonazole-2(3H))-benzyl-methylene diphosphonic acid, having the following formula:

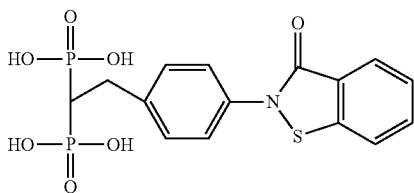 [SMILES: O=c1c2ccccc2sn1-c1ccc(CC(P(=O)(O)O)P(=O)(O)O)cc1]

The diphosphonic acid compound is prepared from the same synthesis process with embodiment 1, but the only difference is that selenium powder is replaced by sulfur powder to obtain yellow solid.

1H-NM (DMSO, δ) 2.11~2.27 (t, 1H); 2.98~3.12 (d, 2H); 7.121~7.325 (d, 2H); 7.352~7.371 (t, 1H); 7.402~7.464 (d, 2H); 7.501~7.592 (t, 1H); 7.610~7.741 (d, 1H); 7.918~8.002 (d, 1H); 10.198~10.693 (S, 4H).

ESI-MS: 415.

Element analysis: S 15.1%, P 14.9%.

It is determined that the yellow solid is 4-(3-carbonylbenzo[d][1,2]sulfonazole-2(3H))-phenylethyl-methylene diphosphonic acid.

Example 16

SC-16

The diphosphonate compound in this embodiment is 4-(3-carbonylbenzo[d][1,2]sulfonazole-2(3H))-benzyl-1-hydroxyl-methylene diphosphonic acid, having the following formula:

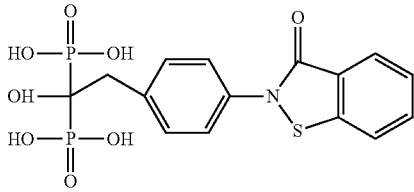 [SMILES: O=c1c2ccccc2sn1-c1ccc(CC(O)(P(=O)(O)O)P(=O)(O)O)cc1]

The diphosphonic acid compound is prepared from the same synthesis process with embodiment 2, but the only difference is that selenium powder is replaced by sulfur powder to obtain yellow solid.

1H-NMR (DMSO, δ) 3.07~3.21 (S, 2H); 7.310~7.332 (d, 2H); 7.350~7.369 (t, 1H); 7.517~7.537 (d, 2H); 7.562~7.593 (t, 1H); 7.614~7.642 (d, 1H); 7.801~7.872 (d, 1H); 9.313 (S, 1H); 10.409 (S, 4H).

ESI-MS: 431.

Element analysis: S 14.6%, P 14.3%.

It is determined that the yellow solid is 4-(3-carbonylbenzo[d][1,2]selenazole-2(3H))-phenylethyl-1-hydroxyl-methylene diphosphonic acid.

Function Test Cases of Diphosphonate Compound

Test drugs: SC-1~16; self-made, referring to the above examples.

Positive control: alendronate sodium (ALEN), National Institutes for Food and Drug Control (batch number: 100901-200601).

Blank: dissolvants except tested drugs or ALEN.

(1) Effects on the Function of Osteoblasts

Cell Culture of Osteoblasts

MG63 osteoblasts (Key Laboratory of Ministry of Education for Biological Therapy of Human Diseases, SCU), after 24 h of recovery, cells adhere to wall and grow, and the endochylema begins to extend, fresh F-12 culture media containing 10% fetal bovine serum is added, and replaced every 48 hours, when cell confluence reaches to 70%-80%, 0.25% trypsin is used for digestion, so that adherent cells become loose and round-shaped, and the digestion liquid is extracted out and added with fresh F-12 culture media containing 10% fetal bovine serum to terminate digestion, and cells are pipetted from the culture flask and adjusted to the desired density, and transferred into the other culture flasks or culture plates.

1) Effect on Osteoblasts Proliferation and Differentiation

MTT method is used to evaluate the effects of the drug on the activity of proliferation of osteoblasts MG63, wherein each well of 96-well plate is added with fresh MTT (5 mg/mL) 100 µL, incubated under 37° C. for 4 h, and vibrated every a period of time, then the supernatant is removed, and each well is added with 200 µL DMSO (DMSO, Sigma corp.), and vibrated on micro-oscillator for 10 min, and equivalent amount of liquid is transferred to an new plate, and the absorbance value under 490 nm is measured, referring to table 1.

TABLE 1

Cell proliferation of each group (MTT method, n = 4, $\bar{x} \pm s$)

| Group | | 24 h | 48 h | 72 h |
|---|---|---|---|---|
| Blank | | 0.383 ± 0.012 | 0.441 ± 0.010 | 0.659 ± 0.012 |
| SC-1 | $10^{-9}$ mol/L | 0.371 ± 0.009 | 0.437 ± 0.008 | 0.746 ± 0.011* |
| | $10^{-7}$ mol/L | 0.337 ± 0.011 | 0.425 ± 0.007 | 0.649 ± 0.010 |
| | $10^{-5}$ mol/L | 0.340 ± 0.009 | 0.398 ± 0.011* | 0.299 ± 0.009** |
| SC-2 | $10^{-9}$ mol/L | 0.365 ± 0.008 | 0.412 ± 0.007 | 0.713 ± 0.013* |
| | $10^{-7}$ mol/L | 0.377 ± 0.006 | 0.431 ± 0.009 | 0.701 ± 0.008 |
| | $10^{-5}$ mol/L | 0.351 ± 0.009 | 0.387 ± 0.005* | 0.317 ± 0.013** |
| SC-3 | $10^{-9}$ mol/L | 0.387 ± 0.012 | 0.413 ± 0.008 | 0.646 ± 0.009 |
| | $10^{-7}$ mol/L | 0.362 ± 0.011 | 0.410 ± 0.011 | 0.587 ± 0.012 |
| | $10^{-5}$ mol/L | 0.332 ± 0.009 | 0.367 ± 0.007* | 0.304 ± 0.005** |
| SC-4 | $10^{-9}$ mol/L | 0.365 ± 0.008 | 0.431 ± 0.008 | 0.755 ± 0.009* |
| | $10^{-7}$ mol/L | 0.341 ± 0.011 | 0.466 ± 0.006 | 0.637 ± 0.011 |
| | $10^{-5}$ mol/L | 0.335 ± 0.007 | 0.411 ± 0.010 | 0.302 ± 0.008** |
| SC-5 | $10^{-9}$ mol/L | 0.371 ± 0.006 | 0.419 ± 0.008 | 0.702 ± 0.009 |
| | $10^{-7}$ mol/L | 0.361 ± 0.008 | 0.437 ± 0.010 | 0.661 ± 0.010 |
| | $10^{-5}$ mol/L | 0.348 ± 0.009 | 0.414 ± 0.007 | 0.383 ± 0.009** |
| SC-6 | $10^{-9}$ mol/L | 0.428 ± 0.010 | 0.441 ± 0.008 | 0.699 ± 0.008 |
| | $10^{-7}$ mol/L | 0.410 ± 0.007 | 0.400 ± 0.007 | 0.632 ± 0.010 |
| | $10^{-5}$ mol/L | 0.392 ± 0.010 | 0.377 ± 0.009* | 0.411 ± 0.008* |
| SC-7 | $10^{-9}$ mol/L | 0.366 ± 0.007 | 0.461 ± 0.008 | 0.631 ± 0.009 |
| | $10^{-7}$ mol/L | 0.346 ± 0.009 | 0.469 ± 0.008 | 0.618 ± 0.009 |
| | $10^{-5}$ mol/L | 0.333 ± 0.010 | 0.412 ± 0.012 | 0.317 ± 0.011** |
| SC-8 | $10^{-9}$ mol/L | 0.355 ± 0.009 | 0.421 ± 0.008 | 0.773 ± 0.013* |
| | $10^{-7}$ mol/L | 0.373 ± 0.010 | 0.439 ± 0.012 | 0.709 ± 0.010 |
| | $10^{-5}$ mol/L | 0.376 ± 0.009 | 0.412 ± 0.007 | 0.342 ± 0.008** |
| SC-9 | $10^{-9}$ mol/L | 0.356 ± 0.008 | 0.431 ± 0.008 | 0.698 ± 0.008 |
| | $10^{-7}$ mol/L | 0.363 ± 0.008 | 0.457 ± 0.010 | 0.713 ± 0.011 |
| | $10^{-5}$ mol/L | 0.347 ± 0.007 | 0.400 ± 0.008* | 0.323 ± 0.010** |
| SC-10 | $10^{-9}$ mol/L | 0.355 ± 0.007 | 0.421 ± 0.009 | 0.698 ± 0.008 |
| | $10^{-7}$ mol/L | 0.359 ± 0.011 | 0.429 ± 0.011 | 0.614 ± 0.011 |
| | $10^{-5}$ mol/L | 0.341 ± 0.007 | 0.387 ± 0.009* | 0.328 ± 0.009** |
| SC-11 | $10^{-9}$ mol/L | 0.366 ± 0.009 | 0.427 ± 0.009 | 0.694 ± 0.009 |
| | $10^{-7}$ mol/L | 0.341 ± 0.009 | 0.438 ± 0.008 | 0.656 ± 0.011 |
| | $10^{-5}$ mol/L | 0.331 ± 0.007 | 0.413 ± 0.012 | 0.322 ± 0.009** |
| SC-12 | $10^{-9}$ mol/L | 0.378 ± 0.008 | 0.442 ± 0.007 | 0.720 ± 0.011 |
| | $10^{-7}$ mol/L | 0.364 ± 0.009 | 0.462 ± 0.008 | 0.712 ± 0.007 |
| | $10^{-5}$ mol/L | 0.359 ± 0.011 | 0.395 ± 0.008* | 0.342 ± 0.009** |
| SC-13 | $10^{-9}$ mol/L | 0.374 ± 0.011 | 0.432 ± 0.007 | 0.661 ± 0.009 |
| | $10^{-7}$ mol/L | 0.359 ± 0.010 | 0.422 ± 0.009 | 0.610 ± 0.010 |
| | $10^{-5}$ mol/L | 0.345 ± 0.008 | 0.385 ± 0.011* | 0.311 ± 0.012** |
| SC-14 | $10^{-9}$ mol/L | 0.377 ± 0.012 | 0.435 ± 0.008 | 0.637 ± 0.009 |
| | $10^{-7}$ mol/L | 0.358 ± 0.010 | 0.426 ± 0.009 | 0.627 ± 0.011 |
| | $10^{-5}$ mol/L | 0.324 ± 0.009 | 0.388 ± 0.008* | 0.324 ± 0.009** |
| SC-15 | $10^{-9}$ mol/L | 0.395 ± 0.007 | 0.462 ± 0.008 | 0.688 ± 0.010 |
| | $10^{-7}$ mol/L | 0.366 ± 0.004 | 0.433 ± 0.006 | 0.524 ± 0.011 |
| | $10^{-5}$ mol/L | 0.331 ± 0.007 | 0.352 ± 0.006** | 0.308 ± 0.007 |

TABLE 1-continued

Cell proliferation of each group (MTT method, $n = 4, \bar{x} \pm s$)

| Group | | 24 h | 48 h | 72 h |
|---|---|---|---|---|
| SC-16 | $10^{-9}$ mol/L | 0.348 ± 0.007 | 0.432 ± 0.008 | 0.612 ± 0.007 |
| | $10^{-7}$ mol/L | 0.343 ± 0.005 | 0.415 ± 0.007 | 0.527 ± 0.011 |
| | $10^{-5}$ mol/L | 0.316 ± 0.007 | 0.324 ± 0.006** | 0.262 ± 0.007** |
| Alen | $10^{-9}$ mol/L | 0.359 ± 0.009 | 0.455 ± 0.007 | 0.673 ± 0.07 |
| | $10^{-7}$ mol/L | 0.351 ± 0.002 | 0.426 ± 0.004 | 0.546 ± 0.012 |
| | $10^{-5}$ mol/L | 0.345 ± 0.009 | 0.339 ± 0.006** | 0.258 ± 0.008** |

*$p < 0.05$, compared with control group;
**$p < 0.01$, compared with control group Table 1 indicates that, compared with the corresponding control groups (including blank and positive control) at the same time points, there is no statistical difference in absorbance value both at 24 h and 48 h ($P>0.05$), indicating the tested drugs and ALEN have no influence on proliferation of MG63 cells in the range of concentrations within 48 h. After 72 h's incubation of the compound, $10^{-9}$ mol/L of SC-1, SC-2, SC-4, SC-8 groups, compared with the corresponding control groups, there are statistical difference in absorbance value ($P<0.05$), indicating the above SC compounds in low concentration when cocultured for 72 h with MG63 could enhance MG63 cell proliferation; ALEN groups in higher concentration of $10^{-5}$, $10^{-7}$ mol/L for 72 h, and cell proliferation activity is inhibited in different degrees (compared with the corresponding control groups, $P<0.01$), but compared with the corresponding control groups, there is an increasing tendency of absorbance value in other SC groups, indicating SC compounds may up-regulate MG63 cell proliferation in certain concentrations; and only when concentration and effecting period of SC reach to $10^{-5}$ mol/L and 72 h respectively, the proliferation activity of MG63 cell is obviously affected ($P<0.01$), indicating high concentrations ($10^{-5}$, $10^{-7}$ mol/L) inhibit MG63 cell proliferation only after a long time (72 h) of effect. Compared with positive control (Alen), each group of tested compound has no statistically difference in MG63 cell inhibition, indicating the inhibition activity of each tested drug is equivalent to Alen.

2) Calcium Deposition Assay (Alizarin Red Method)

The alizarin red S(ARS) quantitative assay is applied, wherein each well of 6 well plate is added with $10^{-5}$ mol/L, $10^{-7}$ mol/L, $10^{-9}$ mol/L of SC or ALEN respectively for 5 d ($1,25$-$(OH)_2VitD_3$ is added 48 h before experiment termination for each well, and the final concentration of the vitamin is $10^{-8}$ mol/L), and the culture media is extracted out, and then the cell was rinsed with PBS (pH7.2) gently for 3 times, fixed in 95% alcohol for 15 min, and stained with 1% alizarin red S under room temperature for 30 min-45 min, and Image Pro Plus 6.0 software (Media Cybernetics Inc.) is applied to measure the size of calcium nodules (orange red, diameter>200 μm). Next, each well is added with 1 mL extract (extract preparation: 800 mL 10% acetic acid with 200 mL anhydrous ethyl alcohol), and extracted for 30 min-45 min, kept in dark, shaken slightly, the absorbance of 450 nm wavelength is measured and recorded. According to the equation $y=0.0088x+0.0549$ (y, absorbance, x, concentration of alizarin red S, μg/mL; $r=0.997$), the concentration of alizarin red S in each well is calculated. As alizarin red S and calcium are linear correlated, the calcium deposition is evaluated according to the alizarin red S concentration. Results are shown in table 2.

TABLE 2

Effect of each group of drugs on mineralization of osteoblasts ($n = 4, \bar{x} \pm s$)

| Group | | calcium nodule size/mm² | ARS concentration (μg/mL) |
|---|---|---|---|
| Blank control | | 1.34 ± 0.17 | 344 ± 25 |
| SC-1 | $10^{-9}$ mol/L | 2.53 ± 0.35** | 455 ± 31 |
| | $10^{-7}$ mol/L | 1.62 ± 0.09* | 389 ± 43 |
| | $10^{-5}$ mol/L | 1.01 ± 0.12 | 277 ± 26 |
| SC-2 | $10^{-9}$ mol/L | 2.47 ± 0.18** | 440 ± 22 |
| | $10^{-7}$ mol/L | 1.99 ± 0.20* | 415 ± 23 |
| | $10^{-5}$ mol/L | 1.01 ± 0.05 | 213 ± 11 |
| SC-3 | $10^{-9}$ mol/L | 2.44 ± 0.13** | 431 ± 19 |
| | $10^{-7}$ mol/L | 1.91 ± 0.17 | 413 ± 21 |
| | $10^{-5}$ mol/L | 1.13 ± 0.03 | 263 ± 10 |
| SC-4 | $10^{-9}$ mol/L | 2.39 ± 0.28** | 463 ± 28 |
| | $10^{-7}$ mol/L | 1.51 ± 0.08 | 401 ± 45 |
| | $10^{-5}$ mol/L | 1.14 ± 0.09 | 297 ± 33 |
| SC-5 | $10^{-9}$ mol/L | 2.03 ± 0.13* | 411 ± 18 |
| | $10^{-7}$ mol/L | 1.87 ± 0.21 | 386 ± 20 |
| | $10^{-5}$ mol/L | 1.27 ± 0.10 | 300 ± 15 |
| SC-6 | $10^{-9}$ mol/L | 2.53 ± 0.19** | 469 ± 17 |
| | $10^{-7}$ mol/L | 2.02 ± 0.16* | 421 ± 18 |
| | $10^{-5}$ mol/L | 1.19 ± 0.04 | 259 ± 12 |
| SC-7 | $10^{-9}$ mol/L | 2.11 ± 0.19** | 416 ± 25 |
| | $10^{-7}$ mol/L | 1.44 ± 0.08 | 332 ± 27 |
| | $10^{-5}$ mol/L | 1.09 ± 0.07 | 277 ± 41 |
| SC-8 | $10^{-9}$ mol/L | 1.96 ± 0.19* | 395 ± 17 |
| | $10^{-7}$ mol/L | 1.66 ± 0.16 | 354 ± 23 |
| | $10^{-5}$ mol/L | 1.32 ± 0.11 | 309 ± 13 |
| SC-9 | $10^{-9}$ mol/L | 2.61 ± 0.27** | 487 ± 15 |
| | $10^{-7}$ mol/L | 2.11 ± 0.13* | 433 ± 19 |
| | $10^{-5}$ mol/L | 1.27 ± 0.07 | 329 ± 12 |
| SC-10 | $10^{-9}$ mol/L | 2.49 ± 0.33** | 460 ± 24 |
| | $10^{-7}$ mol/L | 1.97 ± 0.09* | 411 ± 43 |
| | $10^{-5}$ mol/L | 1.12 ± 0.07 | 265 ± 18 |
| SC-11 | $10^{-9}$ mol/L | 2.38 ± 0.11** | 451 ± 29 |
| | $10^{-7}$ mol/L | 2.01 ± 0.21* | 398 ± 21 |
| | $10^{-5}$ mol/L | 1.21 ± 0.11 | 299 ± 26 |
| SC-12 | $10^{-9}$ mol/L | 2.51 ± 0.17** | 445 ± 30 |
| | $10^{-7}$ mol/L | 1.75 ± 0.16 | 365 ± 26 |
| | $10^{-5}$ mol/L | 0.97 ± 0.02 | 239 ± 12 |
| SC-13 | $10^{-9}$ mol/L | 2.39 ± 0.26** | 447 ± 36 |
| | $10^{-7}$ mol/L | 1.89 ± 0.07 | 419 ± 31 |
| | $10^{-5}$ mol/L | 1.11 ± 0.14 | 291 ± 21 |
| SC-14 | $10^{-9}$ mol/L | 2.01 ± 0.20* | 401 ± 21 |
| | $10^{-7}$ mol/L | 1.87 ± 0.15* | 411 ± 19 |
| | $10^{-5}$ mol/L | 1.17 ± 0.04 | 239 ± 7 |
| SC-15 | $10^{-9}$ mol/L | 1.59 ± 0.17 | 399 ± 26 |
| | $10^{-7}$ mol/L | 1.01 ± 0.05 | 328 ± 20 |
| | $10^{-5}$ mol/L | 0.94 ± 0.03 | 219 ± 11 |
| SC-16 | $10^{-9}$ mol/L | 1.97 ± 0.19* | 395 ± 29 |
| | $10^{-7}$ mol/L | 1.55 ± 0.06 | 313 ± 11 |
| | $10^{-5}$ mol/L | 1.12 ± 0.10 | 288 ± 25 |
| Alen | $10^{-9}$ mol/L | 1.74 ± 0.15 | 381 ± 23 |
| | $10^{-7}$ mol/L | 1.47 ± 0.19 | 325 ± 29 |
| | $10^{-5}$ mol/L | 0.97 ± 0.09 | 183 ± 12 |

*$p < 0.05$, compared with control group;
**$p < 0.01$, compared with control group Results indicate that each SC compound in lower concentration increases the calcium deposition of osteoblasts obviously, especially SC-1, SC-2, SC-4, SC-6, SC-9, SC-10, SC-11, SC-12, SC-13, SC-14, SC-15, but each group of compound of high concentration ($10^{-5}$ mol/L) inhibits calcium deposition of osteoblasts. It is not found that Alen group of low concentration can enhance the calcium deposition of osteoblasts.

(2) Effects on the Function of Osteoclasts

The osteoclasts is cultured using a modified Chambers method, the new-born Japanese White Rabbit (1 week-age, provided by Experimental Animal Center of West China Medical Center of Sichuan University) is sacrificed by neck dislocation, and dipped in 75% ethanol for 5 min, long bones are taken out under sterile condition, and soft tissue, periosteum as well as osteoepiphysis on the bone surface are removed in D-Hanks balanced salt solution, clean the bone shaft with α-MEM 2 times, and then cut off the long bone longitudinally in α-MEM full media (containing 15% fetal calf serum, penicillin 100 U/mL, streptomycin 100 ng/mL, 25 m MHEPES, pH 7.0-7.2), scrape the medullar cavity of the bone gently until it is clean, and use a pipette (5 mL syringe, 25 G syringe needle) to rinse the medullar cavity repeatedly with culture media, and then the rinse solution is collected and filtered with cell strainer to remove bone fragment, and centrifuged at 1000 rpm for 5 min, the precipitate is suspended by 10 mL α-MEM, a hematocytometer is used for cell counting, the cell density in suspension is adjusted to $1 \times 10^7$/mL, and inoculate the cells in 6-well plates, and co-cultured with glass slide or bone slice, after 60 min the culture media was replaced with α-MEM induction culture media (containing 15% fetal bovine serum, 10 nM 1, 25-(OH)$_2$VitD$_3$, penicillin 100 U/mL, streptomycin 100 μg/mL, 25 mM HEPES, pH 7.0-7.2), the culture media is replaced every 3 days.

1) Evaluation the Drugs' Effect on Osteoclasts Cell Formation by Cell Counting

Each group of osteoclasts is performed with tartrate-resistant acid phosphatase (TRAP) staining, observed in optical microscope, and the TRAP staining positive cells are counted. Results are shown in table 3.

TABLE 3

Effect of the drug on OC cell formation (n = 6, $\bar{x} \pm s$)

| Group | | 3 d | 5 d |
|---|---|---|---|
| Blank | | 13 ± 2 | 32 ± 7 |
| SC-1 | $10^{-9}$ mol/L | 12 ± 3 | 15 ± 3 |
| | $10^{-7}$ mol/L | 14 ± 4 | 10 ± 5 |
| | $10^{-5}$ mol/L | 5 ± 1 | 1 ± 1 |
| SC-2 | $10^{-9}$ mol/L | 10 ± 3 | 14 ± 5 |
| | $10^{-7}$ mol/L | 13 ± 5 | 11 ± 4 |
| | $10^{-5}$ mol/L | 8 ± 3 | 3 ± 2 |
| SC-3 | $10^{-9}$ mol/L | 13 ± 5 | 15 ± 6 |
| | $10^{-7}$ mol/L | 9 ± 5 | 4 ± 3 |
| | $10^{-5}$ mol/L | 12 ± 3 | 3 ± 3 |
| SC-4 | $10^{-9}$ mol/L | 13 ± 2 | 13 ± 4 |
| | $10^{-7}$ mol/L | 11 ± 2 | 12 ± 2 |
| | $10^{-5}$ mol/L | 6 ± 2 | 3 ± 1 |
| SC-5 | $10^{-9}$ mol/L | 11 ± 2 | 13 ± 3 |
| | $10^{-7}$ mol/L | 14 ± 5 | 13 ± 6 |
| | $10^{-5}$ mol/L | 9 ± 1 | 7 ± 2 |
| SC-6 | $10^{-9}$ mol/L | 13 ± 1 | 13 ± 4 |
| | $10^{-7}$ mol/L | 11 ± 3 | 7 ± 4 |
| | $10^{-5}$ mol/L | 12 ± 6 | 5 ± 4 |
| SC-7 | $10^{-9}$ mol/L | 12 ± 3 | 21 ± 6 |
| | $10^{-7}$ mol/L | 10 ± 2 | 15 ± 4 |
| | $10^{-5}$ mol/L | 6 ± 2 | 9 ± 2 |
| SC-8 | $10^{-9}$ mol/L | 12 ± 3 | 21 ± 6 |
| | $10^{-7}$ mol/L | 10 ± 2 | 15 ± 4 |
| | $10^{-5}$ mol/L | 6 ± 2 | 9 ± 2 |
| SC-9 | $10^{-9}$ mol/L | 12 ± 7 | 19 ± 7 |
| | $10^{-7}$ mol/L | 10 ± 3 | 14 ± 5 |
| | $10^{-5}$ mol/L | 10 ± 6 | 7 ± 3 |
| SC-10 | $10^{-9}$ mol/L | 13 ± 3 | 20 ± 8 |
| | $10^{-7}$ mol/L | 9 ± 4 | 16 ± 5 |
| | $10^{-5}$ mol/L | 3 ± 3 | 6 ± 5 |
| SC-11 | $10^{-9}$ mol/L | 9 ± 3 | 14 ± 8 |
| | $10^{-7}$ mol/L | 10 ± 7 | 12 ± 6 |
| | $10^{-5}$ mol/L | 5 ± 3 | 8 ± 6 |
| SC-12 | $10^{-9}$ mol/L | 13 ± 2 | 19 ± 6 |
| | $10^{-7}$ mol/L | 10 ± 5 | 14 ± 9 |
| | $10^{-5}$ mol/L | 7 ± 6 | 7 ± 3 |
| SC-13 | $10^{-9}$ mol/L | 12 ± 4 | 11 ± 2 |
| | $10^{-7}$ mol/L | 9 ± 3 | 9 ± 6 |
| | $10^{-5}$ mol/L | 3 ± 1 | 2 ± 1 |
| SC-14 | $10^{-9}$ mol/L | 13 ± 3 | 14 ± 9 |
| | $10^{-7}$ mol/L | 11 ± 6 | 12 ± 4 |
| | $10^{-5}$ mol/L | 7 ± 3 | 5 ± 1 |

TABLE 3-continued

Effect of the drug on OC cell formation (n = 6, $\bar{x} \pm s$)

| Group | | 3 d | 5 d |
|---|---|---|---|
| SC-15 | $10^{-9}$ mol/L | 12 ± 5 | 13 ± 3 |
| | $10^{-7}$ mol/L | 10 ± 3 | 11 ± 5 |
| | $10^{-5}$ mol/L | 8 ± 3 | 7 ± 3 |
| SC-16 | $10^{-9}$ mol/L | 11 ± 5 | 15 ± 6 |
| | $10^{-7}$ mol/L | 9 ± 4 | 12 ± 3 |
| | $10^{-5}$ mol/L | 8 ± 3 | 6 ± 2 |
| Alen | $10^{-9}$ mol/L | 14 ± 6 | 18 ± 6 |
| | $10^{-7}$ mol/L | 13 ± 4 | 15 ± 5 |
| | $10^{-5}$ mol/L | 8 ± 2 | 5 ± 2 |

*$p < 0.05$, compared with blank;
**$p < 0.01$, compared with blank

Results indicate that all concentrations of SC compounds and Alen, compared with blank, can inhibit the formation of osteoclasts, and the inhibition is depending on the incubation time and concentrations of the tested drugs, but there is no significant difference between SC compounds and Alen, indicating SC compounds and Alen have equivalent inhibition effect on the formation of osteoclasts. Generally, with the concentration and incubation time of the drugs increasing, TRAP$^+$ cell number obviously decreases.

2) Observation of Osteoclastic Absorption

After 5 days' culture of osteoclasts, the bone slices were taken out, fixed in 2.5% glutaraldehyde for 7 min, cleaned by ultrasonic agitation for 5 min in 0.25 mmol/L ammonium hydroxide 3 times, dehydrated with alcohol and air-dried, stained with 1% toludine blue (containing 1% sodium borate) for 3 min, air-dried, images are photographed with Nikon IX60 microscope, using SPOT Cool CCD camera, the size of resorption pit on the whole bone slices is detected using Image Pro Plus 6.0 software. Results are shown in table 4.

TABLE 4

Effect of the drugs on formation and size of resorption pit of the osteoclast (n = 6, $\bar{x} \pm s$)

| Drug concentration/mol/L | $10^{-9}$ | $10^{-7}$ | $10^{-5}$ |
|---|---|---|---|
| Blank group | 154.60 ± 12.47 | | |
| SC-1 | 98.92 ± 7.26 | 59.16 ± 11.85 | 8.73 ± 1.75 |
| SC-2 | 91.23 ± 8.31 | 43.52 ± 7.59 | 10.42 ± 2.16 |
| SC-3 | 100.49 ± 10.15 | 59.49 ± 10.03 | 9.35 ± 1.09 |
| SC-4 | 90.51 ± 9.07 | 64.59 ± 8.87 | 8.42 ± 2.25 |
| SC-5 | 98.41 ± 13.26 | 46.40 ± 11.21 | 5.58 ± 0.98 |
| SC-6 | 109.43 ± 16.42 | 68.43 ± 9.92 | 10.13 ± 2.78 |
| SC-7 | 103.45 ± 9.67 | 72.53 ± 9.83 | 8.50 ± 2.11 |
| SC-8 | 118.25 ± 14.73 | 64.45 ± 8.77 | 12.23 ± 3.06 |
| 5C-9 | 107.23 ± 9.88 | 45.72 ± 7.86 | 11.12 ± 2.65 |
| SC-10 | 96.53 ± 8.54 | 48.55 ± 9.32 | 10.52 ± 3.33 |
| SC-11 | 99.53 ± 11.27 | 56.72 ± 10.11 | 9.43 ± 4.25 |
| SC-12 | 112.99 ± 16.39 | 82.23 ± 13.39 | 10.04 ± 1.86 |
| SC-13 | 112.11 ± 9.96 | 92.45 ± 12.28 | 11.52 ± 2.64 |
| 5C-14 | 96.37 ± 8.72 | 79.79 ± 9.04 | 8.80 ± 2.31 |
| 5C-15 | 99.37 ± 8.43 | 81.92 ± 9.12 | 9.17 ± 3.47 |
| SC-16 | 88.76 ± 6.23 | 69.02 ± 15.61 | 13.01 ± 1.17 |
| Alen | 107.77 ± 8.37 | 65.02 ± 18.77 | 10.81 ± 1.02 |

The results show that the resorption pits size of all tested drugs groups as well as Alen groups decrease obviously compared with blank ($p<0.01$), indicating both SC compounds and Alen have inhibition effect on osteoclasts; the highest concentration ($10^{-5}$ mol/L) of drugs, including Alen, present the maximal reduction in resorption pits size, and there are no significant differences between SC groups and Alen groups in resorption pits size, indicating the tested drugs perform equivalent effect on the inhibition of osteoclasts with Alen.

The current in vitro study indicates that, the bisphosphonates SC: on one hand, may inhibit differentiation and maturation of osteoclasts, and reduce the metabolic activity of bone resorption; on the other hand, they may also considerably promote proliferation and differentiation of osteoblasts, enhance bone formation and regulate metabolic balance of bone formation/resorption, finally, restore the homeostasis of bone.

The in vitro study shows that the invention of SC compounds characteristic by their proliferation promotion effect to osteoblasts as well as the bisphosphonates' inhibition effect to osteoclasts. Therefore, the SC compounds of the present invention perform dual-directional regulation effect for osteoporosis treatment.

The invention claimed is:

1. A compound with formula II:

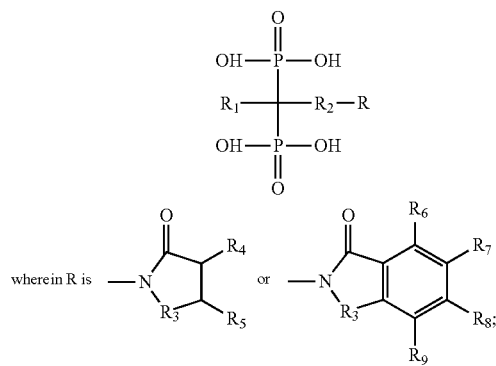

II $R_1$ is H, OH or halogen;
$R_2$ is —$(CH_2)_{n1}$—Ar—$(CH_2)_{n2}$— or —$(CH_2)_{n3}$—, $n_1=1\sim10$, $n_2=0\sim10$, and $n_3=1\sim10$; if $n_1$, $n_2$ or $n_3 \geq 1$, the $(CH_2)_{n1}$, $(CH_2)_{n2}$ or $(CH_2)_{n3}$ may be substituted by halogen, —CN, —$NO_2$ or —OH; Ar is arylene or arylene substituted with $C_1$-$C_6$ alkyl, $C_1$-$C_6$ substituted alkyl, halogen, —CN, —$NO_2$ or —OH;
$R_3$ is Se or S;
$R_4$ and $R_5$ are independently selected from the group consisting of hydrogen, halogen, —CN, —$NO_2$, —OH, —OR', —COOR', —OCOOR', —COR', —CON(R')$_2$, —OCON(R')$_2$, —SR, —$SO_2R$, —$SO_2N(R')_2$, an —SOR' group, $C_1$-$C_{10}$ alkyl, $C_1$-$C_{10}$ substituted alkyl, alkenyl, substituted alkenyl, alkynyl, substituted alkynyl aryl or substituted aryl, wherein each of R and R' is independently selected from the group consisting of H, alkyl, aryl, substituted alkyl or substituted alkyl; or $R_4$ and $R_5$ constitute 3-7 carbons of cyclo alkane, the cyclo alkane may be substituted by $C_1$-$C_6$ alkyl, $C_1$-$C_6$ substituted alkyl, halogen, —CN, —$NO_2$ or —OH;
$R_6$, $R_7$, $R_8$ and $R_9$ are independently selected from the group consisting of Hydrogen, halogen, —CN, —$NO_2$, —OH, —OR', —COOR', —OCOOR', —COR', —CON(R')$_2$, —OCON(R')$_2$, —SR, —$SO_2R$, —$SO_2N(R')_2$, an —SOR' group, alkyl, alkenyl, alkynyl, aryl, substituted alkyl, substituted alkenyl, substituted alkynyl or substituted aryl, wherein each of R and R' is independently selected from H, alkyl, aryl, substituted alkyl or substituted aryl.

2. The compound according to claim 1, characterized in that $R_1$ is H, OH or halogen;

$R_2$ is —$(CH_2)_{n1}$—Ar—$(CH_2)_{n2}$— or —$(CH_2)_{n3}$—, wherein $n_1=1\sim10$, $n_2=0\sim10$, $n_3=1\sim10$; Ar is arylene or arylene substituted with halogen, —CN, —$NO_2$ or —OH;
$R_3$ is Se or S;
$R_4$ and $R_5$ are independently selected from the group consisting of Hydrogen, halogen, —CN, —$NO_2$, —OH or $C_1$-$C_{10}$ alkyl;
$R_6$, $R_7$, $R_8$ and $R_9$ are each independently selected from the group consisting of Hydrogen, halogen, —CN, —$NO_2$ or —OH alkyl.

3. The compound according to claim 2, characterized in that $R_1$ is H or OH.

4. The compound according to claim 2, characterized in that $R_1$ is halogen.

5. The compound according to claim 4, characterized in that $R_1$ is F, Cl or Br.

6. The compound according to claim 2, characterized in that $R_2$ is —$(CH_2)_{n1}$—Ar—$(CH_2)_{n2}$— or —$(CH_2)_{n3}$—, wherein $n_1=1\sim4$, $n_2=0\sim1$, $n_3=1\sim5$; Ar is arylene or arylene substituted with halogen, —CN, —$NO_2$ or —OH.

7. The compound according to claim 2, characterized in that $R_2$ is —$(CH_2)_{n1}$—Ar—$(CH_2)_{n2}$— or —$(CH_2)_{n3}$—, and Ar is arylene.

8. The compound according to claim 7, characterized in that $R_2$ is —$(CH_2)_{n1}$—Ar—$(CH_2)_{n2}$— or —$(CH_2)_{n3}$—, wherein Ar is phenylene.

9. The compound according to claim 2, characterized in that $R_3$ is Se.

10. The compound according to claim 2, characterized in that $R_6$, $R_7$, $R_8$ and $R_9$ are hydrogen.

11. The compound according to claim 2, characterized in that
$R_1$ is H or OH;
$R_2$ is —$(CH_2)_{n1}$—Ar—$(CH_2)_{n2}$— or —$(CH_2)_{n3}$—, wherein $n_1=1$-4, $n_2=0$-1, $n_3=1$-5, and Ar is arylene;
$R_3$ is Se;
$R_4$ and $R_5$ are independently selected from the group consisting of Hydrogen, halogen, —CN, —$NO_2$ or —OH; and
$R_6$, $R_7$, $R_8$ and $R_9$ are hydrogen.

12. A method for preparing a compound according to claim 1, comprising the following steps:
(1). Proton activation of methylene:
Tetraisopropylmethylenediphosphonate and NaH are reacted for 1 h-4 h under −5° C.-40° C., with the mole ratio of NaH and tetraisopropylmethylendiphosphonate being 1:1-3:1;
(2). alkylation reaction:
a compound of the formula Br—$R_2$—$NO_2$ is added to a reaction liquid from step (1) to perform an alkylation reaction under 60° C. ~150° C. for 2 h~5 h, wherein the mole ratio of Br—$R_2$—$NO_2$ and tetraisopropylmethylenediphosphonate is 1:1-3:1; after reaction, organic solvent is added to the reaction liquid for extraction, an organic phase is collected and evaporated to dryness, and a compound of the formula $(((CH_3)_2CHO)_2P(=O))_2 CHR_2NO_2$ is obtained;
(3). reduction of nitro:
10% Pd/C catalyst is added to an alcohol solution of the compound $(((CH_3)_2CHO)_2P(=O))_2CHR_2NO_2$ and hydrogen gas is inlet, reacted under room temperature with 0.1 MPa-2 MPa of Hydrogen pressure in reaction system for 18 h-48 h, with the weight ratio of the compound $(((CH_3)_2CHO)_2P(=O))_2CHR_2NO_2$ and 10% Pd/C catalyst being 1:0.5-1:5, then a compound of the formula $(((CH_3)_2CHO)_2P(=O))_2CHR_2NH_2$ is obtained after filtering and evaporating to dryness;

(4). cyclization:

an alkaline solution is added to the compound $(((CH_3)_2CHO)_2P(=O))_2CHR_2NH_2$ under the temperature of −20° C.~−5° C., the pH is regulated to 7~14, and then an organic solvent and a compound of the formula IV:

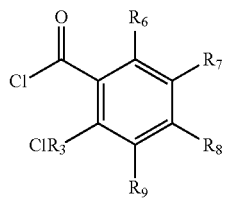

IV are added, under room temperature, for 3 h~8 h, with the mole ratio of $(((CH_3)_2CHO)_2P(=O))_2CHR_2NH_2$ to the compound of the formula IV being 1:1-1:5, and a reaction solution thereof is filtered, a precipitate is collected and washed with an organic solvent, and dried under 60° C.-100° C. for 4 h-24 h to obtain a compound of the formula $(((CH_3)_2CHO)_2P(=O))_2CHR_2R$, where R is

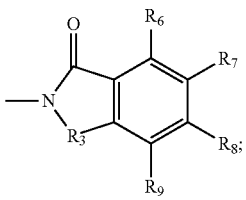

(5). hydrolysis:

an alcohol and concentrated hydrochloric acid are added to the compound of the formula $(((CH_3)_2CHO)_2P(=O))_2CHR_2R$ in a ratio of 1 g of the compound of the formula $(((CH_3)_2CHO)_2P(=O))_2CHR_2R$ to 5 mL~50 mL of the alcohol solution and 5 mL~60 mL of the concentrated hydrochloric acid, refluxed under 90° C.~120° C. for 4 h~10 h, and evaporated, washed with alcohol, and an obtained solid is vacuum-dried under 50° C.~120° C. for 4 h~10 h, to obtain the diphosphonate compound having formula II where R is

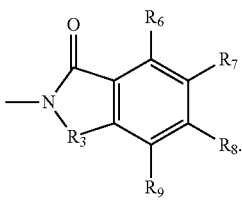

13. The method according to claim 12, characterized in that the organic solvent in step (2) is methylene dichloride, methenyl chloride, ethyl acetate or petroleum ether.

14. The method according to claim 12, characterized in that the alkaline solution in step (4) is NaHCO₃ solution.

15. The method compound according to claim 12, characterized in that the organic solvent of step (4) is ethyl ether, methylene dichloride, methenyl chloride or ethyl acetate.

16. A method for preparing a compound according to claim 1, comprising the following steps:

(1). cyclization:

a solution of a compound of the formula IV:

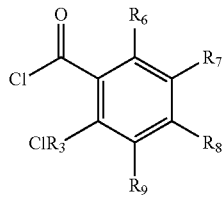

IV is added to an ω-amino acid methyl ester of the formula $CH_3C(=O)-R_2-NH_2$, and reacted under room temperature at pH 7~14 for 3 h~8 h, with a mole ratio of the compound of the formula IV and the ω-amino acid methyl ester being 1:1~3:1, a reaction liquid thereof is filtered, and a resulting precipitate is washed with an organic solvent and dried under 50° C.~100° C. for 4 h~24 h, to obtain a compound of the formula $CH_3C(=O)-R_2-R$, where R is

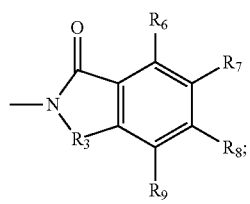

(2). hydrolysis:

an alcohol and hydrochloric acid are added to the compound of the formula $CH_3C(=O)-R_2-R$ in a ratio of 1 g of the compound of the formula $CH_3C(=O)-R_2-R$ to 2 mL~50 mL of the alcohol and 5 mL-50 mL of the hydrochloric acid, refluxed under 90° C.~120° C. for 4 h-10 h, and a solvent is removed through reduced pressure distillation, and a residue thereof is recrystallized to obtain a compound of the formula $HOC(=O)-R_2-R$;

(3). phosphoration:

the compound of the formula $HOC(=O)-R_2-R$ is reacted with phosphorous acid and phosphorus trichloride under 90° C.~120° C. for 2 h~6 h, water is added to a reaction product, with 1 g of the compound of the formula $HOC(=O)-R_2-R$ added for each 1 mL~50 mL water, and refluxed under 90° C.~110° C. for 1 h~3 h, with a mole ratio of the compound of the formula $HOC(=O)-R_2-R$ and phosphorous acid being 1:1~1:5, and a mole ratio of the compound of the formula $HOC(=O)-R_2-R$ and phosphorus trichloride being 1:2~1:6, and a reaction liquid thereof is filtered, an alcohol solution is added to a filtrate thereof and kept at −5° C.~−5° C. for 12 h~48 h; then the alcohol solution and filtrate are suction-filtered, washed with water, and vacuum-dried under 50° C.~120° C. for 4 h~10 h, to obtain the diphosphonate compound with formula II, where R is

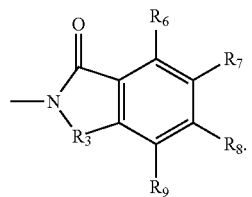

17. The method for preparing the compound according to claim 16, characterized in that the solution in step (1) includes a solvent selected from ethyl ether, methylene dichloride, methenyl chloride and ethyl acetate.

18. The method according to claim 12, wherein the compound of the formula IV is o-seleniumchloroylbenzoyl chloride or o-sulfachloroylbenzoyl chloride.

19. The method according to claim 16, wherein the compound of the formula IV is o-seleniumchloroylbenzoyl chloride or o-sulfachloroylbenzoyl chloride.

* * * * *